(12) United States Patent
Takahashi et al.

(10) Patent No.: US 11,473,058 B2
(45) Date of Patent: Oct. 18, 2022

(54) METHOD FOR INDUCING DOPAMINERGIC NEURON PROGENITOR CELLS

(71) Applicants: KYOTO UNIVERSITY, Kyoto (JP); OSAKA UNIVERSITY, Suita (JP); EISAI R&D MANAGEMENT CO., LTD., Tokyo (JP)

(72) Inventors: Jun Takahashi, Kyoto (JP); Daisuke Doi, Kyoto (JP); Bumpei Samata, Kyoto (JP); Kiyotoshi Sekiguchi, Suita (JP); Yuichi Ono, Kobe (JP)

(73) Assignees: Kyoto University, Kyoto (JP); Osaka University, Osaka (JP); Eisai R&D Management Co., Ltd., Tokyo (JP)

( * ) Notice: Subject to any disclaimer, the term of this patent is extended or adjusted under 35 U.S.C. 154(b) by 190 days.

(21) Appl. No.: 14/916,696

(22) PCT Filed: Sep. 4, 2014

(86) PCT No.: PCT/JP2014/073372
§ 371 (c)(1),
(2) Date: Mar. 4, 2016

(87) PCT Pub. No.: WO2015/034012
PCT Pub. Date: Mar. 12, 2015

(65) Prior Publication Data
US 2016/0215260 A1    Jul. 28, 2016

(30) Foreign Application Priority Data
Sep. 5, 2013   (JP) .............................. JP2013-184387

(51) Int. Cl.
*A61K 35/30*    (2015.01)
*C12N 5/0797*   (2010.01)
*C12N 5/0793*   (2010.01)

(52) U.S. Cl.
CPC ............ *C12N 5/0623* (2013.01); *A61K 35/30* (2013.01); *C12N 5/0619* (2013.01); *C12N 2501/119* (2013.01); *C12N 2501/13* (2013.01); *C12N 2501/15* (2013.01); *C12N 2501/155* (2013.01); *C12N 2501/41* (2013.01); *C12N 2501/415* (2013.01); *C12N 2501/727* (2013.01); *C12N 2506/02* (2013.01); *C12N 2506/03* (2013.01); *C12N 2506/45* (2013.01); *C12N 2533/52* (2013.01)

(58) Field of Classification Search
CPC .................................................. C12N 5/0623
See application file for complete search history.

(56) References Cited

U.S. PATENT DOCUMENTS

| 2006/0211109 A1 | 9/2006 | Totey et al. |
| 2007/0254281 A1 | 11/2007 | Ono et al. |
| 2008/0199437 A1 | 8/2008 | Sakamoto et al. |
| 2011/0008769 A1 | 1/2011 | Ono et al. |
| 2011/0217774 A1 | 9/2011 | Kim et al. |
| 2012/0178083 A1 | 7/2012 | Ono et al. |
| 2012/0252021 A1 | 10/2012 | Ono et al. |
| 2015/0299654 A1 | 10/2015 | Sakamoto et al. |

FOREIGN PATENT DOCUMENTS

| JP | 2006-521807 | 9/2006 |
| KR | 10-2011-0050310 | 5/2011 |
| WO | 2005/052190 | 6/2005 |
| WO | 2006/009241 | 1/2006 |
| WO | 2007/119759 | 10/2007 |
| WO | WO 2012/162124 | 11/2012 |
| WO | 2013/015457 | 1/2013 |

OTHER PUBLICATIONS

Kirkeby et al. (frontiers in Cellular Neuroscience, 6(64): 1-4, 2012. (Year: 2012).*
Schulz et al, (Stem Cells, 22:1218-1238, 2004) (Year: 2004).*
Berry (Cells Tissues Organs 2018; 205: 331-349) (Year: 2018).*
Dakhore (Stem Cells International, vol. 2018, 1-18, 2018) (Year: 2018).*
Shibata (Cell Reports, 25: 1668-1679, 2018) (Year: 2018).*
Sart (Eng Life Sci, 1-14, 2021) (Year: 2021).*
Office Action in Australian Patent Application No. 2014316100, dated Nov. 15, 2019, 5 pages.
Doi D. et al., "Isolation of Human Induced Pluripotent Stem Cell-Derived Dopaminergic Progenitors by Cell Sorting for Successful Transplantation", Stem Cell Reports, vol. 2, pp. 337-350 (2014).
Hwang D.Y. et al., "Human ES and iPS Cells as Cell Sources for the Treatment of Parkinson's Disease: Current State and Problems", Journal of Cellular Biochemistry, vol. 109, pp. 292-301 (2010).
International Search Report for PCT/JP2014/073372 dated Dec. 9, 2014.
Jönsson M.E. et al., "Identification of transplantable dopamine neuron precursors at different stages of midbrain neurogenesis", Experimental Neurology, vol. 219, pp. 341-354 (2009).
Miyazaki T. et al., "Laminin E8 fragments support efficient adhesion and expansion of dissociated human pluripotent stem cells", Nature Communications, vol. 3, No. 1236, pp. 1-10 (2012).

(Continued)

*Primary Examiner* — Anoop K Singh
*Assistant Examiner* — Magdalene K Sgagias
(74) *Attorney, Agent, or Firm* — Fish & Richardson P.C.

(57) ABSTRACT

The present invention provides a method for producing dopaminergic neuron progenitor cells from pluripotent stem cells, which method comprises the steps of: (i) performing adherent culture of pluripotent stem cells on an extracellular matrix in a medium containing a reagent(s) selected from the group consisting of BMP inhibitor, TGFβ inhibitor, SHH signal-stimulating agent, FGF8, and GSK3β inhibitor; (ii) collecting Corin- and/or Lrtm1-positive cells from the cells obtained in Step (i) using a substance which binds to Corin and/or a substance which binds to Lrtm1; and (iii) performing suspension culture of the cells obtained in Step (ii) in a medium containing a neurotrophic factor.

8 Claims, 19 Drawing Sheets
Specification includes a Sequence Listing.

(56) References Cited

OTHER PUBLICATIONS

Wernig M., et al., "Neurons derived from reprogrammed fibroblasts functionally integrate into the fetal brain and improve symptoms of rats with Parkinson's disease", PNAS, vol. 105, No. 15, pp. 5856-5861 (2008).
Response to Office Action in Chinese Patent Application 201480059803. 2, dated May 7, 2019, 13 pages (with English Translation).
Response to Office Action filed in EP Application No. 14841854.4, dated Mar. 26, 2018, 23 pages.
Office Action issued in Japanese Application No. 2015-535520, dated Aug. 28, 2018, 7 pages (with English machine translation).
Decision of Refusal in Japanese Patent Application No. 2015-535520, dated Feb. 5, 2019, 4 pages (with English Translation).
Extended European Search Report in European Application No. 14841854.4 dated Feb. 16, 2017, 13 pages.
Samata et al., "Purification of functional human ES and iPSC-derived midbrain dopaminergic progenitors using LRTM1," Nature Communications, 7:1-11 ncomms 13097 (2016).
Office Action in Chinese Patent Application No. 201480059803.2, dated Nov. 28, 2018, 16 pages (with English translation).
Response to European Search Report in European Application No. 14841854.4, dated Sep. 14, 2017, 80 pages.
Response to Office Action in Chinese Patent Application No. 201480059803.2, dated Dec. 31, 2019, 16 pages (with English Translation).
Zheng, "Comparison of Different Culture Mode for Long-term Expansion of Neural Stem Cells," Master's Thesis of Dalian University of Technology, 2005, 50 pages (Full English Translation only).
Office Action in Chinese Patent Application No. 201480059803.2, dated Aug. 21, 2019, 17 pages (with English Translation).
Sun, "Biological characteristics of neural precursor cells cultured by suspension and adherence methods and influence of ethanol on the expression of connexin-43 in neural precursor cells," Shandong University Master's Thesis, 2010, 67 pages (with Partial English Translation).
Zheng, "Comparison of Different Culture Mode for Long-term Expansion of Neural Stem Cells," Masteral Dissertation, Dalian University of Technology, 2005, 76 pages (with Partial English Translation).
International Preliminary Report on Patentability in Application No. PCT/JP2014/073372, dated Mar. 17, 2016, 8 pages.
Office Action issued in European Application No. 14841854.4 dated Nov. 20, 2017, 12 pages.
Office Action issued in Japanese Patent Application No. 2019-085612, dated Jun. 2, 2020, 8 pages (with Machine Translation).
Office Action issued in Malaysian Patent Application No. PI 2016700764, dated Apr. 28, 2020, 3 pages.
Decision of Rejection in Chinese Patent Application No. 201480059803. 2, dated Jun. 29, 2020, 10 pages (with English Translation).
Office Action issued in Korean Patent Application No. 10-2016-7006591, dated Jun. 29, 2020, 18 pages (with English Translation).
Response to Office Action in Australian Patent Application No. 2014316100, dated Jun. 24, 2020, 11 pages.
Response to Office Action in Malaysian Patent Application No. PI2016700764, dated Jun. 26, 2020, 61 pages.
Office Action in Canadian Patent Application No. 2923592, dated Aug. 7, 2020, 4 pages.
Response to Office Action in Japanese Patent Application No. 2019-085612, dated Sep. 30, 2020, 23 pages (with Machine Translation).
Response to Office Action in Canadian Patent Application No. 2,923,592, dated Dec. 4, 2020, 16 pages.
Response to Office Action in Korean Patent Application No. 10-2016-7006591, dated Nov. 26, 2020, 46 pages (with Machine Translation).
Response to Office Action in Australian Patent Application No. 2014316100, dated Oct. 6, 2020, 12 pages.
Response to Office Action in Chinese Patent Application No. 201480059803.2, dated Oct. 12, 2020, 18 pages (with English Translation).
Office Action issued in Malaysian Patent Application No. PI 2016700764, dated Dec. 15, 2020, 2 pages.
Notice of Reasons for Refusal in Japanese Patent Application No. 2019-085612, dated Jan. 26, 2021, 6 pages (with Machine Translation).
Response to Office Action in Malaysian Patent Application No. PI 2016700764, dated Jan. 15, 2021, 4 pages.
Office Action in Australian Patent Application No. 2014316100, dated Jul. 15, 2020, 4 pages.
Response to Office Action in Japanese Patent Application No. 2019-085612, dated Mar. 8, 2021, 12 pages (with Machine Translation).
Decision to Refuse in Korean Patent Application No. 10-2016-7006591, dated Apr. 29, 2021, 12 pages (with English Translation).
Response to Office Action in Canadian Patent Application No. 2,923,592, dated Dec. 10, 2021, 11 pages.
Response to Office Action in Korean Patent Application No. 10-2016-7006591, dated Jul. 29, 2021, 49 pages (with Machine Translation).
Office Action in Canadian Patent Application No. 2923592, dated Aug. 10, 2021, 6 pages.
Correia et al., "Stem cell-based therapy for Parkinson's disease," Annals of Medicine. 2005, 37(7):487-498.
Office Action in Canadian Patent Application No. 2923592, dated Jun. 2, 2022, 6 pages.
Doi et al., "Prolonged maturation culture favors a reduction in the tumorigenicity and the dopaminergic function of human ESC-derived neural cells in a primate model of Parkinson's disease," Stem Cells, 2012, 30(5):935-945.
Notice of Reasons for Refusal in Japanese Patent Application No. 2021-131135, dated Aug. 23, 2022, 11 pages (with Machine Translation).
Yoshikawa et al., "Systemic administration of valproic acid and zonisamide promotes differentiation of induced pluripotent stem cell-derived dopaminergic neurons," Frontiers in Cellular Neuroscience, 2013, 7(11), 10 pages.

* cited by examiner

Fig. 5
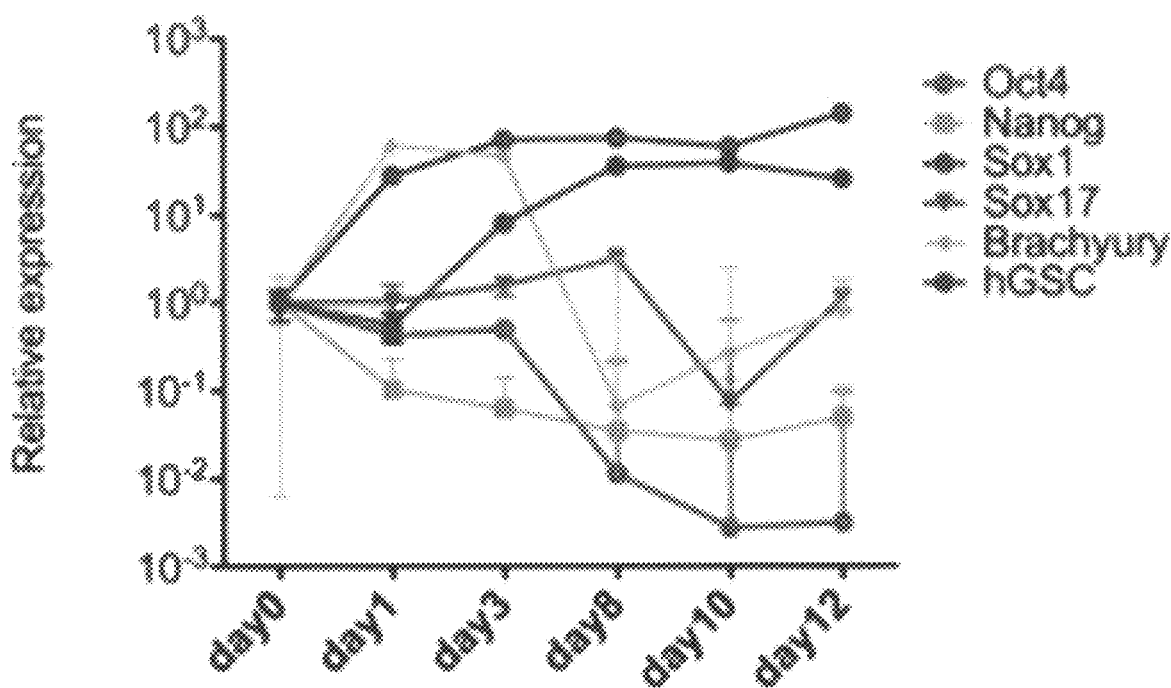
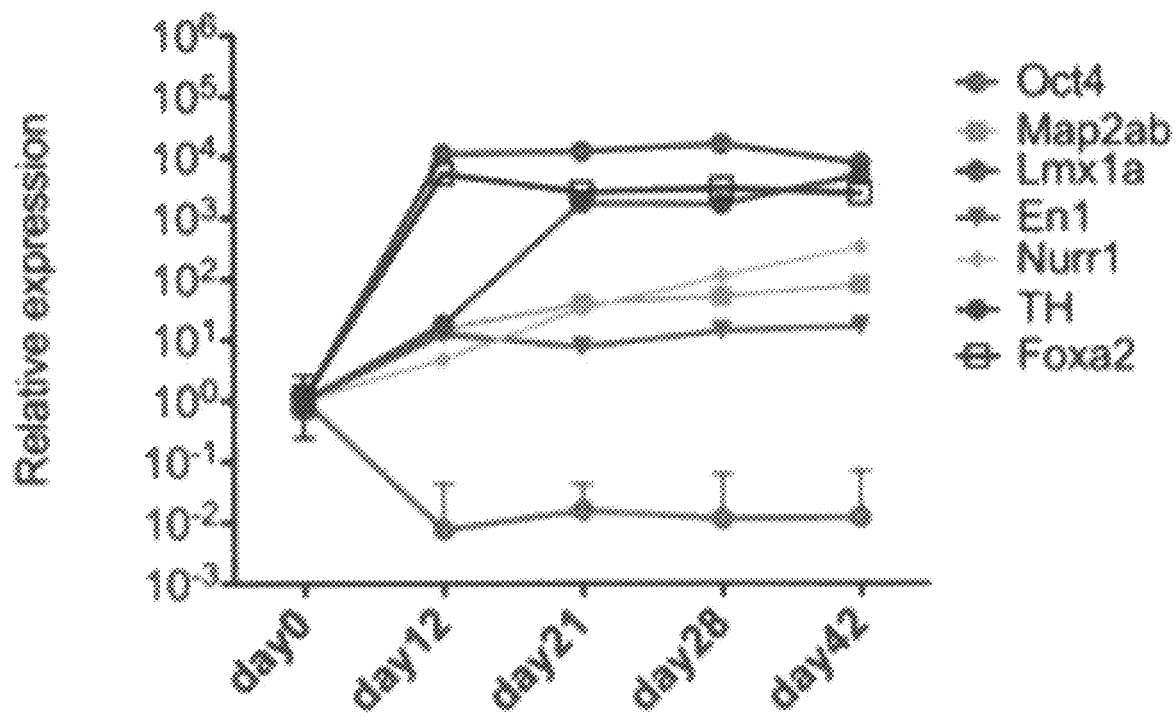

Fig. 7
A
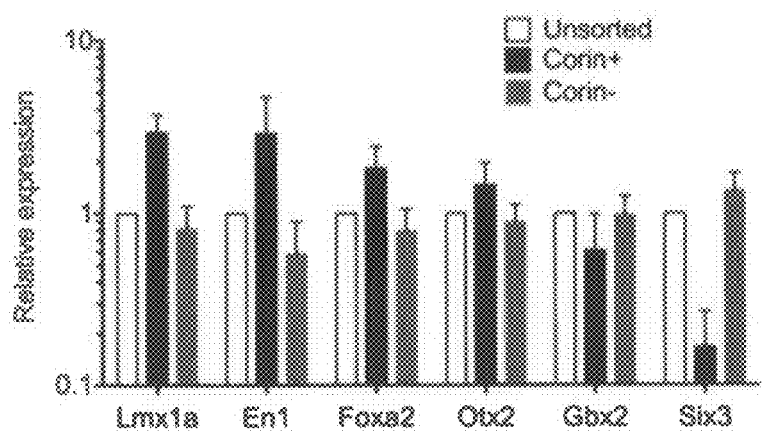
B
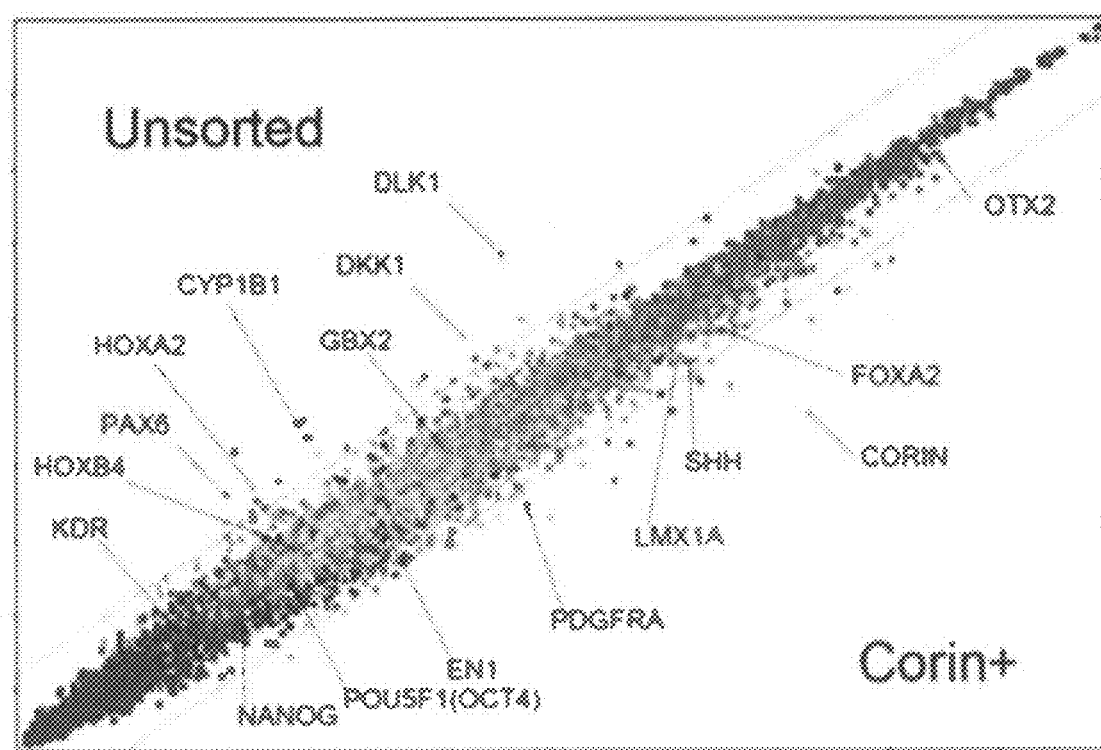

Fig. 9
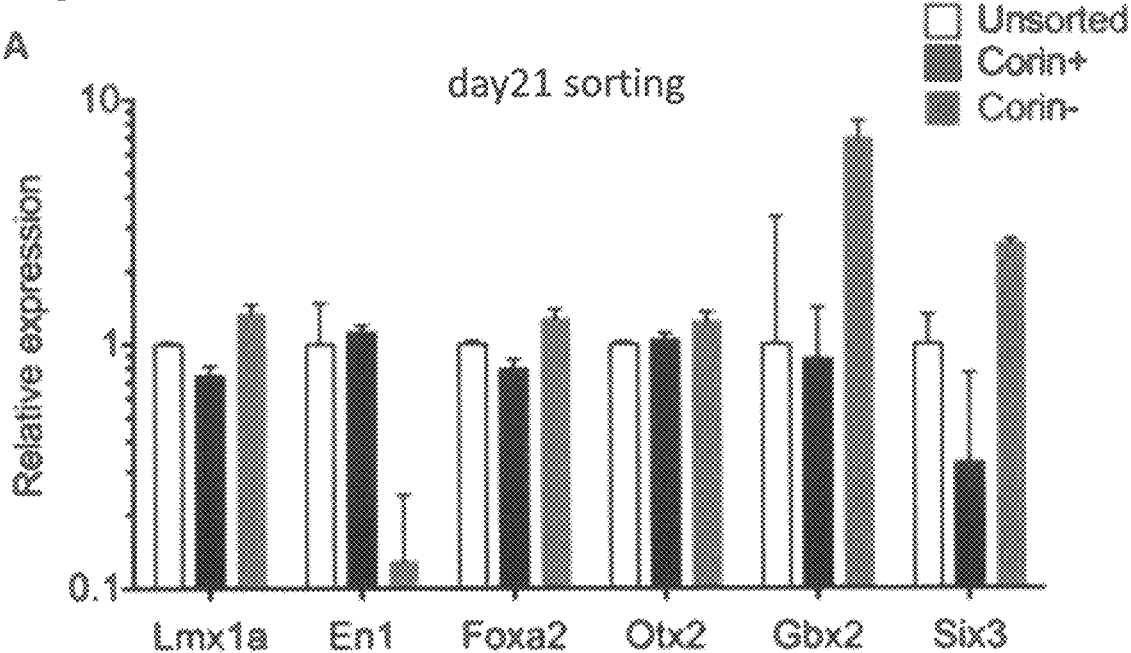
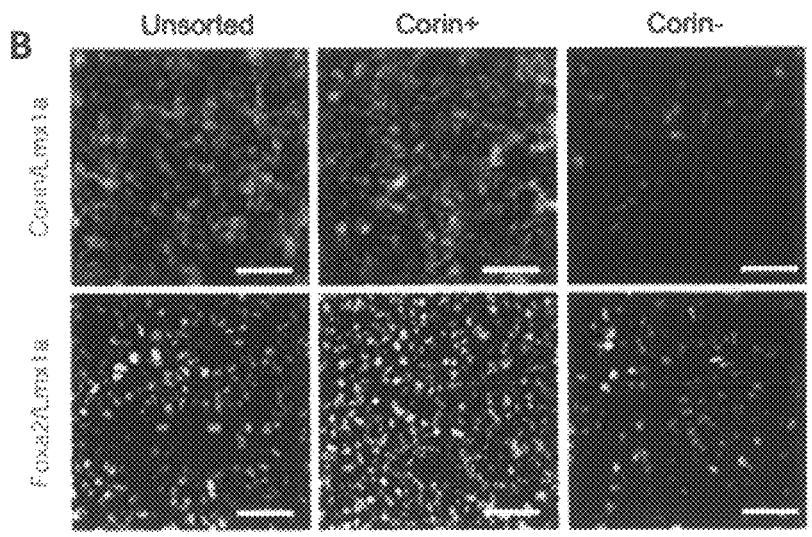
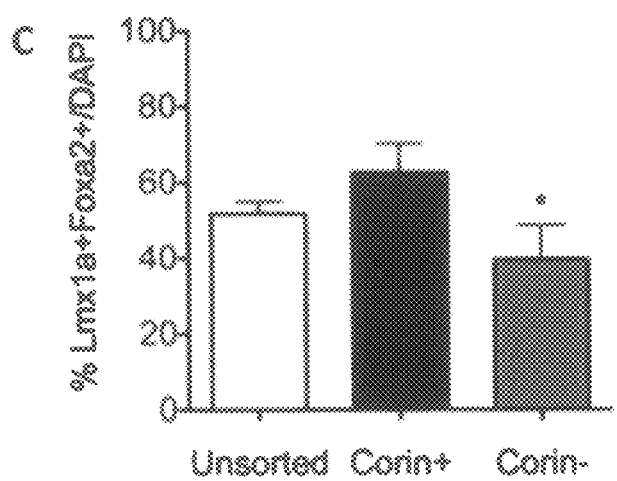

Fig. 10
A
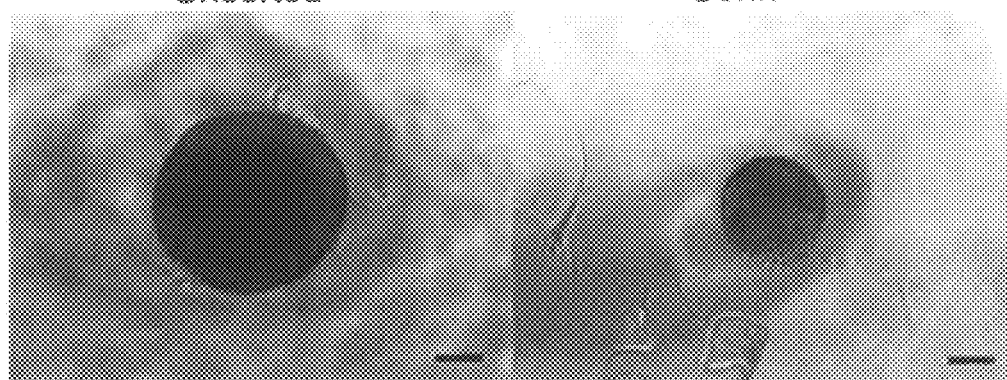
Day 28
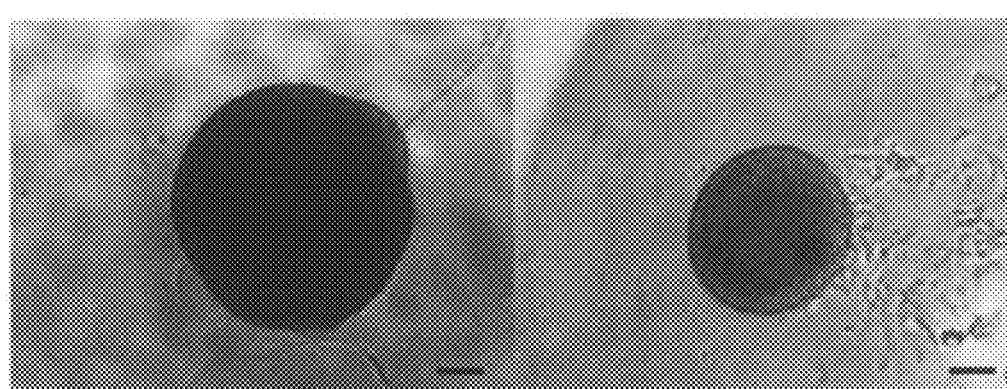
Day 42
B
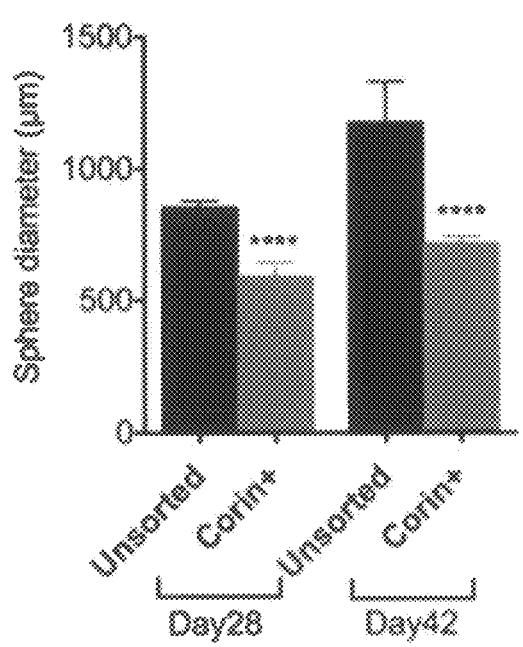

Fig. 13
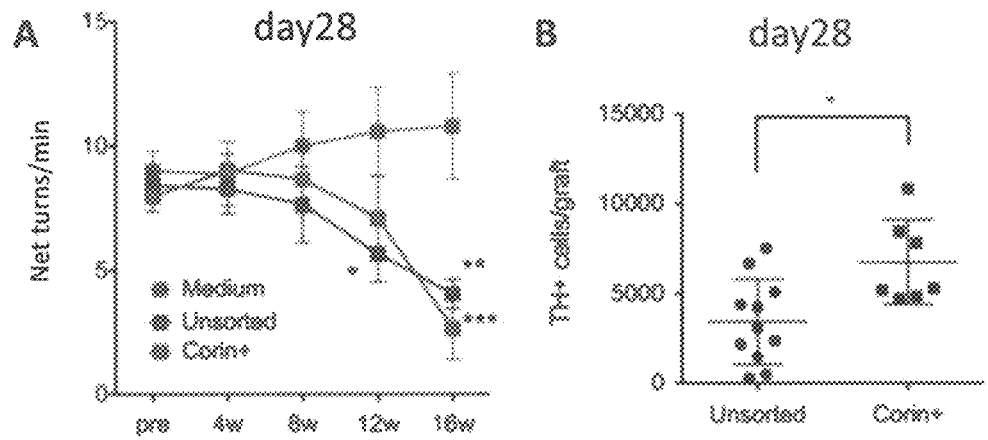
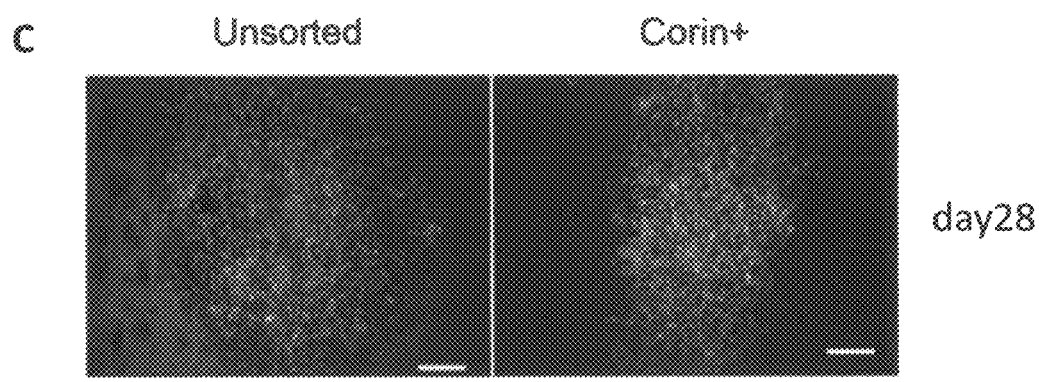
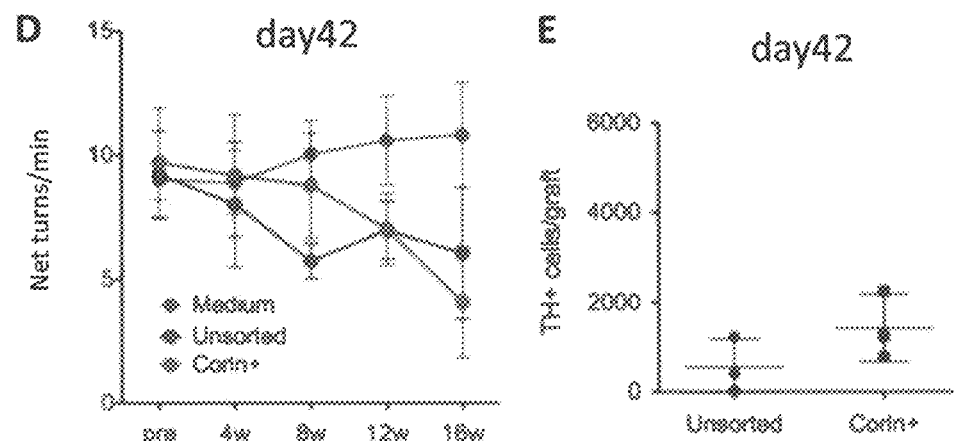
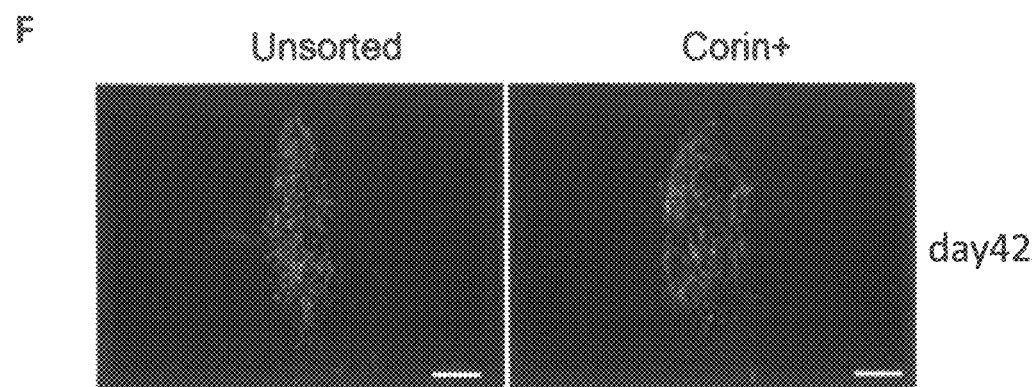

Fig. 16
A
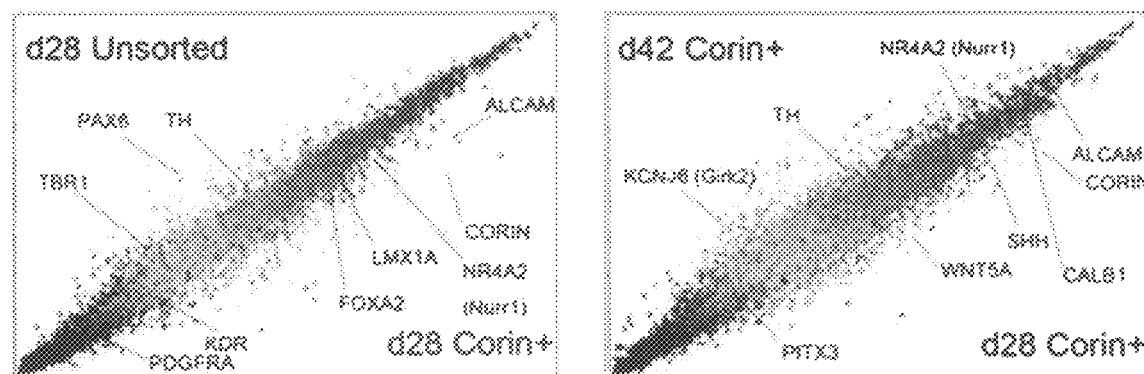
B
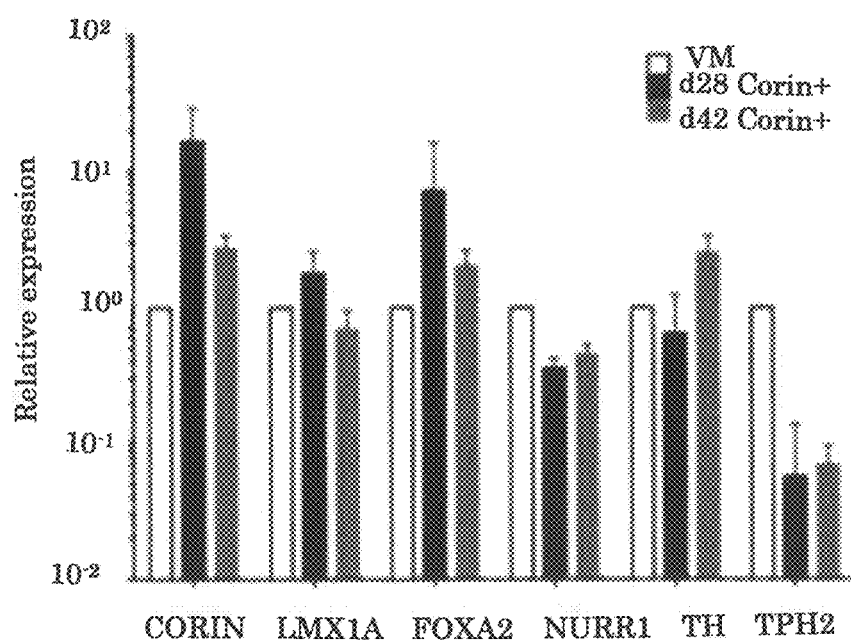
C
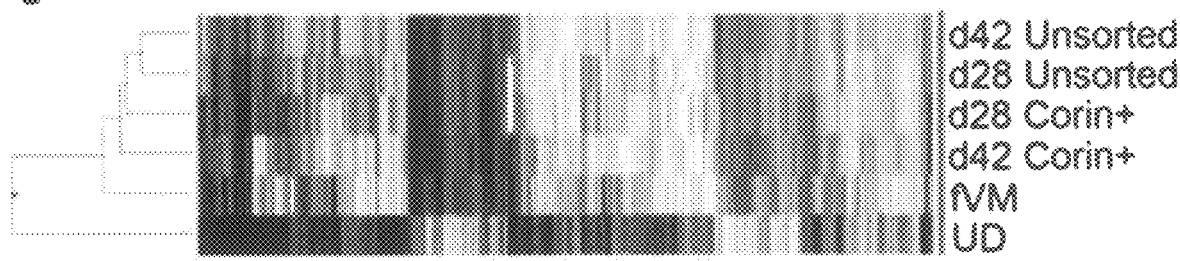

Fig. 17
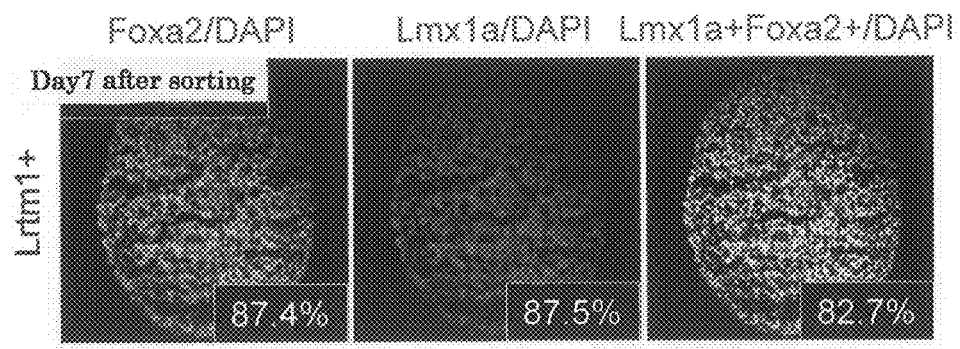
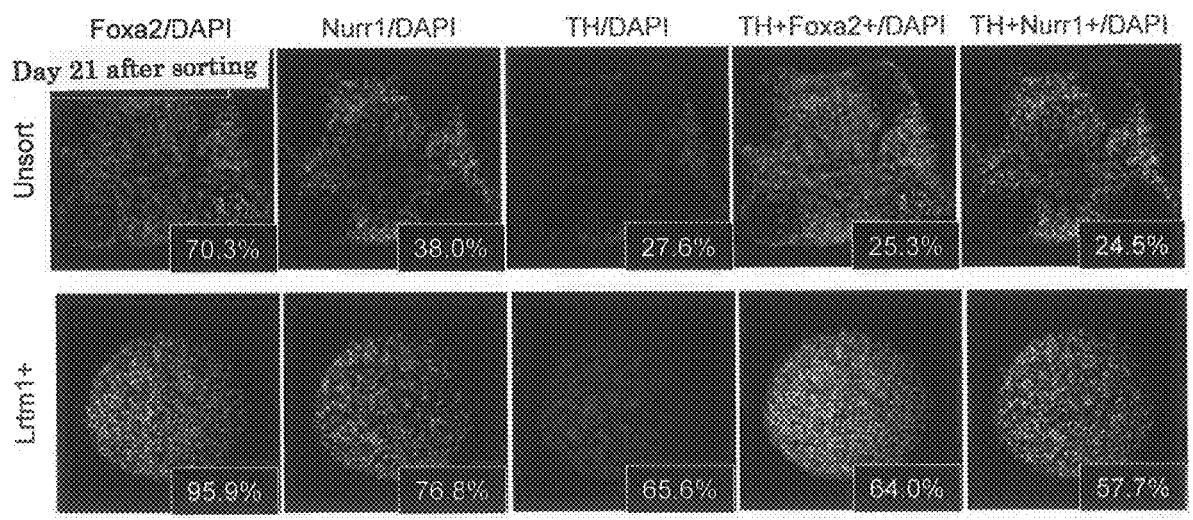

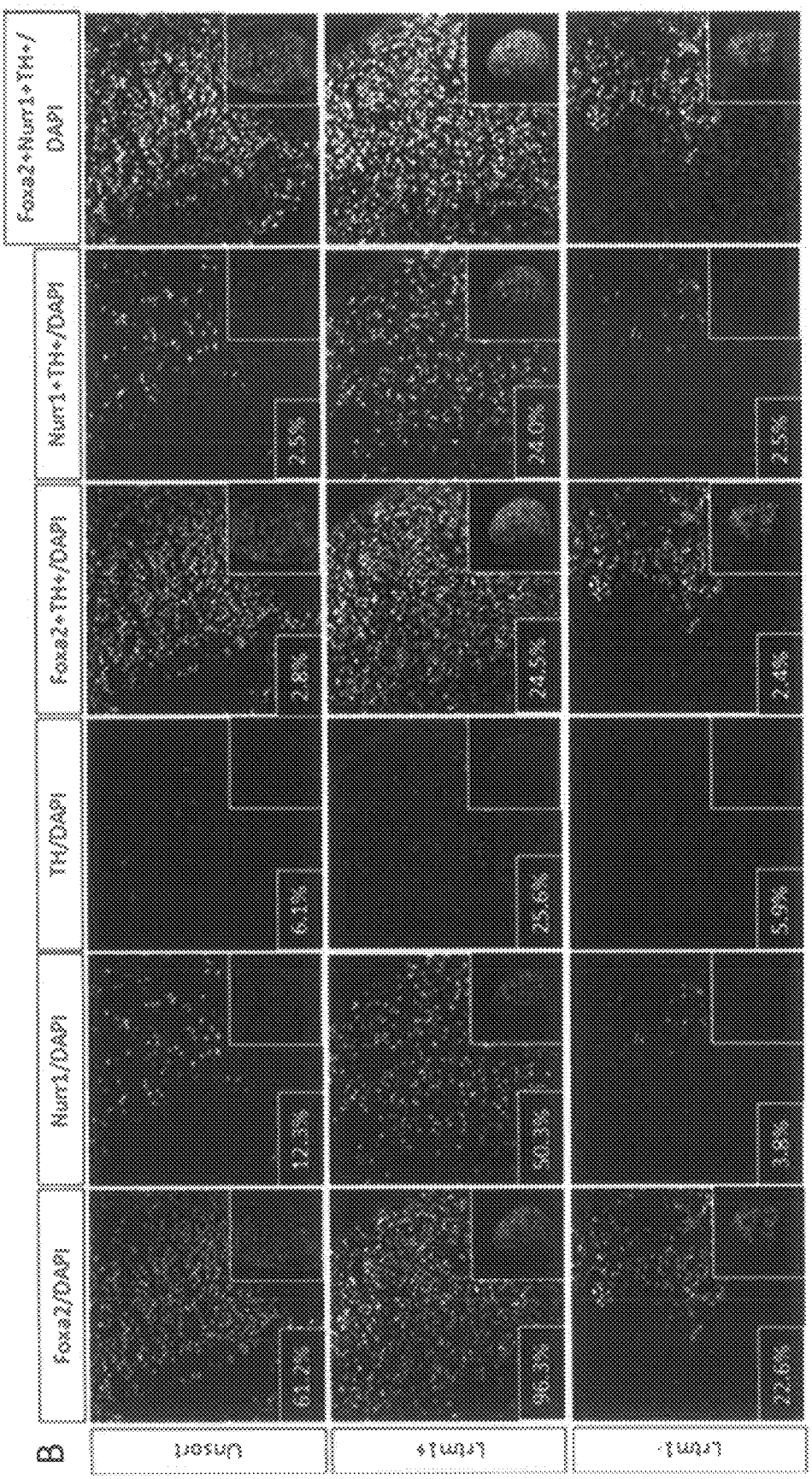

SEQUENCE LISTING

```
<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: L803-mts
<220> FEATURE:
<221> NAME/KEY: MISC_FEATURE
<222> LOCATION: (1)..(1)
<223> OTHER INFORMATION: N-myristoyl glycine
<220> FEATURE:
<221> NAME/KEY: MISC_FEATURE
<222> LOCATION: (11)..(11)
<223> OTHER INFORMATION: phosphorylated serine
<220> FEATURE:
<221> NAME/KEY: MISC_FEATURE
<222> LOCATION: (12)..(12)
<223> OTHER INFORMATION: C-amidated proline
```

```
<400> SEQUENCE: 1

Gly Lys Glu Ala Pro Pro Ala Pro Pro Gln Ser Pro
1               5                   10
```

METHOD FOR INDUCING DOPAMINERGIC NEURON PROGENITOR CELLS

TECHNICAL FIELD

The present invention relates to a method for producing dopaminergic neuron progenitor cells.

BACKGROUND ART

Parkinson's disease is a neurodegenerative disease caused by loss of dopaminergic neural cells in the mesencephalic substantia nigra, and about 4 million people in the world are currently suffering from this disease. For treatment of Parkinson's disease, pharmacotherapy with L-DOPA or a dopamine agonist; coagulation or deep brain stimulation by stereotaxy; fetal mesencephalic grafting; or the like has been carried out.

Fetal mesencephalic grafting is problematic from an ethical point of view because of its source of supply, and the risk of infection is high in this treatment. Thus, a therapeutic method using neural cells prepared by differentiation induction from pluripotent stem cells such as embryonic stem cells (ES cells) or induced pluripotent stem cells (iPS cells) has been proposed (Non-patent Document 1). However, it has been pointed out that transplantation of neural cells prepared by differentiation induction may cause formation of a benign tumor, and dyskinesia which is thought to be due to cells other than the dopaminergic neural cells of interest. Therefore, selection of safe cells that can survive has been demanded for the transplantation.

Under such circumstances, selection of cells suitable for transplantation using marker genes for dopaminergic neural cells or dopaminergic neuron progenitor cells has been proposed (Patent Documents 1 to 4). However, these methods still need improvement in the process of selection of markers. Moreover, whether administration of cells immediately after the selection is preferred, or administration of cells induced from these intermediate cells is preferred, has not been discussed in these documents.

The methods for producing dopaminergic neural cells may still need to be improved also from the viewpoint of reducing the influence of lot-to-lot variability due to biological components contained therein, and suppressing increases in the prices.

PRIOR ART DOCUMENTS

Patent Documents

Patent Document 1: WO 2005/052190
Patent Document 2: WO 2006/009241
Patent Document 3: WO 2007/119759
Patent Document 4: WO 2013/015457

Non-Patent Document

Non-patent Document 1: Wernig M, et al., Proc Natl Acad Sci USA. 2008, 105: 5856-5861

SUMMARY OF THE INVENTION

An object of the present invention is to produce dopaminergic neuron progenitor cells which are preferred as a therapeutic agent for Parkinson's disease. Thus, the present invention aims to provide a production process for dopaminergic neuron progenitor cells, or a kit necessary for the production.

In order to solve the above-described problems, the present inventors focused attention on cell surface membrane proteins Corin and Lrtm1, which are thought to be marker genes for dopaminergic neuron progenitor cells. The present inventors discovered that, by extracting cells using Corin and/or Lrtm1 as an index/indices and culturing the cells followed by their transplantation, the dopamine-producing cells can survive after the transplantation. The present inventors thus found that dopaminergic neuron progenitor cells as a therapeutic agent for Parkinson's disease can be obtained by this production process, thereby completed the present invention.

The present invention relates to the followings:

[1] A method for producing dopaminergic neuron progenitor cells from pluripotent stem cells, said method comprising the steps of:

(i) performing adherent culture of pluripotent stem cells on an extracellular matrix in a medium containing a reagent(s) selected from the group consisting of BMP inhibitor, TGFβ inhibitor, SHH signal-stimulating agent, FGF8, and GSK3β inhibitor;

(ii) collecting Corin- and/or Lrtm1-positive cells from the cells obtained in Step (i); and (iii) performing suspension culture of the cells obtained in Step (ii) in a medium containing a neurotrophic factor.

[2] The method according to [1], wherein said extracellular matrix is laminin 511 or a fragment thereof.

[3] The method according to [2], wherein said laminin 511 is laminin 511E8.

[4] The method according to any one of [1] to [3], wherein Step (i) comprises the steps of:

(a) performing adherent culture of pluripotent stem cells on an extracellular matrix in a medium containing BMP inhibitor and TGFβ inhibitor;

(b) performing adherent culture of the cells obtained in Step (a) on an extracellular matrix in a medium containing BMP inhibitor, TGFβ inhibitor, SHH signal-stimulating agent, and FGF8;

(c) performing adherent culture of the cells obtained in Step (b) on an extracellular matrix in a medium containing BMP inhibitor, TGFβ inhibitor, SHH signal-stimulating agent, FGF8, and GSK3β inhibitor; and (d) performing adherent culture of the cells obtained in Step (c) on an extracellular matrix in a medium containing BMP inhibitor and GSK3β inhibitor.

[5] The method according to any one of [1] to [4], wherein said BMP inhibitor is LDN193189.

[6] The method according to any one of [1] to [4], wherein said TGFβ inhibitor is A83-01.

[7] The method according to any one of [1] to [4], wherein said SHH signal-stimulating agent is Purmorphamine.

[8] The method according to any one of [1] to [4], wherein said GSK3β inhibitor is CHIR99021.

[9] The method according to any one of [1] to [8], wherein said neurotrophic factor is BDNF and GDNF.

[10] The method according to any one of [1] to [9], wherein the medium in Step (iii) further comprises B27 supplement, ascorbic acid, and dibutyryl cyclic AMP.

[11] The method according to any one of [1] to [10], wherein the medium in Step (i) and/or Step (iii) further comprises ROCK inhibitor.

[12] The method according to [11], wherein the ROCK inhibitor is Y-27632.

[13] The method according to any one of [1] to [12], wherein said Step (i) is carried out for at least 10 days.

[14] The method according to any one of [1] to [13], wherein said Step (i) is carried out for 12 days to 21 days.

[15] The method according to any one of [1] to [13], wherein said Step (i) is carried out for 12 days to 14 days.

[16] The method according to any one of [1] to [15], wherein said Step (iii) is carried out for at least 7 days.

[17] The method according to any one of [1] to [16], wherein said Step (iii) is carried out for 14 days to 30 days.

[18] The method according to any one of [1] to [17], wherein said Step (iii) is carried out for 14 days to 16 days.

[19] The method according to any one of [1] to [18], wherein said substance which binds to Corin or said substance which binds to Lrtm1 is an antibody or an aptamer which binds to Corin or Lrtm1.

[20] Dopaminergic neuron progenitor cells obtained by the method according to any one of [1] to [19].

[21] A therapeutic agent for Parkinson's disease, comprising dopaminergic neuron progenitor cells obtained by the method according to any one of [1] to [19].

[22] A kit for preparing dopaminergic neuron progenitor cells from pluripotent stem cells, said kit comprising BMP inhibitor, TGFβ inhibitor, SHH signal-stimulating agent, FGF8, GSK3β inhibitor, extracellular matrix, and neurotrophic factor.

[23] The kit according to [22], further comprising an anti-Corin antibody and/or anti-Lrtm1 antibody.

[24] The kit according to [22] or [23], wherein said extracellular matrix is laminin 511E8.

[25] The kit according to any one of [22] to [24], wherein said BMP inhibitor is LDN193189.

[26] The kit according to any one of [22] to [25], wherein said TGFβ inhibitor is A83-01.

[27] The kit according to any one of [22] to [26], wherein said SHH signal-stimulating agent is Purmorphamine.

[28] The kit according to any one of [22] to [27], wherein said GSK3β inhibitor is CHIR99021.

[29] The kit according to any one of [22] or [28], wherein said neurotrophic factor is BDNF and GDNF.

Effect of the Invention

According to the present invention, dopaminergic neuron progenitor cells which are useful for therapeutic agents for Parkinson's disease and the like and suitable for transplantation, and have a high survival rate, can be efficiently obtained.

BRIEF DESCRIPTION OF THE DRAWINGS

FIG. 5 shows changes in the expression levels of undifferentiation markers and differentiation markers. Each value is represented as a relative value with respect to the value on Day 0, which is taken as 1. On Day 12 in FIG. 5A, values for Sox1, hGSC, Sox17, Brachyury, Nanog, and Oct4 are shown. On Day 42 in FIG. 5B, values for Lmx1a, TH, Foxa2, Nurr1, Map2ab, En1, and Oct4 are shown.

FIG. 7 shows results of analysis of gene expression on Day 12 (day12) in Corin-positive cells and Corin-negative cells obtained by sorting using an anti-Corin antibody, and unsorted cells. FIG. 7A shows the expression levels of Lmx1a, En1, Foxa2, Otx2, Gbx2, and Six3 in each type of cells. Each expression level is represented as a relative value with respect to the value observed for the unsorted cells (unsorted), which is taken as 1. FIG. 7B shows results of microarray analysis for comparison of expression between unsorted cells (unsorted) and Corin-positive cells (Corin$^+$) on Day 12.

FIG. 8A shows trichrome staining images (photographs) for Foxa2/Lmx1a (upper panels) and Otx2/Lmx1a/DAPI (lower panels) in each type of cells. FIG. 8B shows the proportion of Foxa2-positive/Lmx1a-positive cells in each type of cells. FIG. 8C shows the proportion of Otx2-positive/Lmx1a-negative cells in each type of cells. FIG. 8D shows the expression levels of Oct4 and Nanog in each type of cells, and in the cells before the differentiation induction.

FIG. 9 shows results of analysis of gene expression on Day 21 in Corin-positive cells (Corin$^+$) and Corin-negative cells (Corin$^-$) obtained by sorting using an anti-Corin antibody, and unsorted cells (unsorted). FIG. 9A shows the expression levels of Lmx1a, En1, Foxa2, Otx2, Gbx2, and Six3 in each type of cells. Each expression level is represented as a relative value with respect to the value observed for the unsorted cells (unsorted), which is taken as 1. FIG. 9B shows double-staining images (photographs) for Corin/Lmx1a (upper panel) and Foxa2/Lmx1a (lower panels) in each type of cells. FIG. 9C shows the proportion of Foxa2-positive/Lmx1a-positive cells in each type of cells.

FIG. 10 shows results of analysis of the sizes of cell clusters (spheres) on Day 28 (day28) and Day 42 (day42) after the differentiation induction. FIG. 10A shows phase-contrast images (photographs) of the cell clusters. FIG. 10B shows a graph showing the diameters of the cell clusters.

FIG. 11A shows immunostaining images (photographs) for Foxa2/DAPI and Nurr1/TH (tyrosine hydroxylase). FIG. 11B shows the proportions of Nurr1-positive cells, Foxa2-positive cells, and TH-positive cells on Day 28 (left panel) and Day 42 (right panel). FIG. 11C shows the amounts of dopamine (DA), 3,4-dihydroxyphenyl acetic acid (DOPAC), and serotonin (5-HT) released from $1 \times 10^6$ Corin$^+$ cells or unsorted cells on Day 42.

FIG. 12A shows immunostaining images (photographs) of GFAP and Ki67, and human nuclei in the transplants. Magnified images are separately provided for the areas surrounded by frames. FIGS. 12B, 12C, and 12D show graphs prepared by plotting the sizes of the transplants in cases of transplantation of cells on Day 28, Day 42, and Day 19, respectively. FIG. 12E shows the proportions of Ki67-positive cells in the transplants in the cases of transplantation of cells on Day 28.

FIG. 13 shows results of intracerebral transplantation of cells obtained by culturing Corin-positive cells collected by sorting (day 12) (Corin$^+$), cells induced without sorting (Unsorted), or a negative control (Medium), to rats (to which 6-OHDA was administered) on Day 28 (day28) or Day 42 (day42) after the differentiation induction. FIG. 13A shows the number of times of circling behavior per unit time in each period after the transplantation of the cells on Day 28. FIG. 13B shows a graph prepared by plotting the number of TH-positive cells per transplant in the cases of administration of the cells on Day 28. FIG. 13C shows immunostaining images (photographs) of TH (red) and human nuclei (green) in brain in the cases of administration of the cells on Day 28. FIG. 13D shows the number of times of circling behavior per unit time in each period after the transplantation of the cells on Day 42. FIG. 13E shows a graph prepared by plotting the number of TH-positive cells per transplant in the cases of administration of the cells on Day 42. FIG. 13F shows immunostaining images (photographs) of TH (red) and human nuclei (green) in brain in the cases of administration of the cells on Day 42.

FIG. 14A shows a graph prepared by plotting the number of TH-positive cells per neural cell (NauN$^+$). FIG. 14B shows a graph prepared by plotting the number of TH-positive cells per donor cell (human nuc$^+$). FIG. 14C shows double-staining images (photographs) for Foxa2/TH, Pitx3/TH, Nurr1/TH, and Girk2/TH in transplants.

FIG. 15A shows a double-staining image (photograph) for serotonin (green)/TH (red) in a transplant of each type of cells at Week 16. FIG. 15B shows the proportion of serotonin-positive cells among surviving cells (NeuN-positive cells) at Week 16, which proportion was investigated for each type of cells.

FIG. 16 shows results of analysis of gene expression in cells on Day 28, cells on Day 42, and fetal ventral mesencephalic cells. FIG. 16A shows a result of comparison of the expression between cells subjected to sorting for Corin-positive cells on Day 12 (d28 Corin$^+$) and unsorted cells (d28 Unsorted) (left panel), and a result of comparison of the expression between cells on Day 28 after the induction (d28 Corin$^+$) and cells on Day 42 after the induction, which cells on Day 28 and Day 42 had been sorted for Corin-positive cells (right panel). Each comparison was made using a microarray. FIG. 16B shows results of measurement of CORIN, LMX1A, FOXA2, NURR1, TH, and TPH2 in the cells on Day 28 (d28 Corin$^+$), the cells on Day 42 (d42 Corin$^+$), and the fetal ventral mesencephalic cells (VM) using PCR. Each value is shown as a relative value with respect to the value for the fetal ventral mesencephalic cells (VM), which is taken as 1. FIG. 16C shows a result of cluster analysis of the microarray data for the cells on Day 28 which had been sorted for Corin-positive cells (d28 Corin$^+$), unsorted cells on Day 28 (d28 Unsorted), sorted cells on Day 42 (d42 Corin$^+$), unsorted cells on Day 42 (d42 Unsorted), and fetal ventral mesencephalic cells (VM).

FIG. 17 shows staining images of cells obtained by culturing Lrtm1-positive cells collected by sorting (Day 14). FIG. 17A shows images (photographs) obtained by staining with Foxa2 and/or Lmx1a, and DAPI seven days after the sorting. The number in each panel represents the proportion of positive cells. In the case of double staining, the number represents the proportion of double-positive cells. FIG. 17B shows staining images (photographs) for markers (Foxa2, Nurr1, and TH) taken after 21 days of culture of cells sorted for Lrtm1-positive cells (Lrtm1$^+$) or unsorted cells (Unsort). The number in each panel represents the proportion of positive cells. In the cases of double staining, each number represents the proportion of double-positive cells.

FIG. 19-1 shows staining images of cells obtained by collecting Lrtm1-positive cells by sorting and further culturing the collected cells (the images are arranged to show, from left to right, Foxa2/DAPI, Nurr1/DAPI, TH/DAPI, Foxa2$^+$TH$^+$/DAPI, Nurr1$^+$TH$^+$/DAPI, and Foxa2$^+$Nurr1$^+$TH$^+$/DAPI). The number in each panel represents the proportion of positive cells in the staining image. This figure shows staining images of cells which were prepared by sorting on Day 14 of the differentiation induction and culturing of the sorted cells for 7 days thereafter.

FIG. 19-2 shows staining images of cells obtained by collecting Lrtm1-positive cells by sorting and further culturing the collected cells (the images are arranged to show, from left to right, Foxa2/DAPI, Nurr1/DAPI, TH/DAPI, Foxa2$^+$TH$^+$/DAPI, Nurr1$^+$TH$^+$/DAPI, and Foxa2$^+$Nurr1$^+$TH$^+$/DAPI). The number in each panel represents the proportion of positive cells in the staining image. This figure shows staining images of cells which were prepared by sorting on Day 14 of the differentiation induction and culturing of the sorted cells for 14 days thereafter.

FIG. 19-3 shows staining images of cells obtained by collecting Lrtm1-positive cells by sorting and further culturing the collected cells (the images are arranged to show, from left to right, Foxa2/DAPI, Nurr1/DAPI, TH/DAPI, Foxa2$^+$TH$^+$/DAPI, Nurr1$^+$TH$^+$/DAPI, and Foxa2$^+$Nurr1$^+$TH$^+$/DAPI). The number in each panel represents the proportion of positive cells in the staining image. This figure shows staining images of cells which were prepared by sorting on Day 21 of the differentiation induction and culturing of the sorted cells for 7 days thereafter.

EMBODIMENTS FOR CARRYING OUT THE INVENTION

Figure 1:
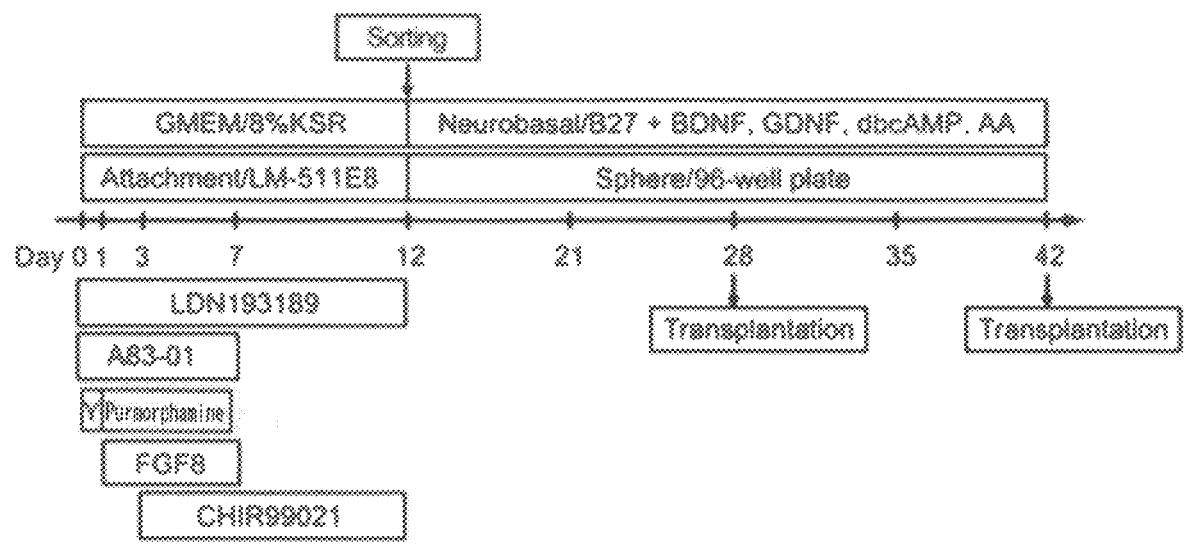
FIG. 1 shows an example of the protocol for producing dopaminergic cells. "Y" represents Y-27632, and "AA" represents ascorbic acid.

The present invention provides a method for producing dopaminergic neuron progenitor cells from pluripotent stem cells, which method comprises the steps of:

(i) performing adherent culture of pluripotent stem cells on an extracellular matrix in a medium containing a reagent(s) selected from the group consisting of BMP inhibitor, TGFβ inhibitor, SHH signal-stimulating agent, FGF8, and GSK3β inhibitor;

(ii) collecting Corin- and/or Lrtm1-positive cells from the cells obtained in the Step (i); and (iii) performing suspension culture of the cells obtained in Step (ii) in a medium containing a neurotrophic factor.

<Pluripotent Stem Cells>

The pluripotent stem cells which may be used in the present invention are stem cells having pluripotency which enables the cells to differentiate into any cells existing in the living body, which pluripotent stem cells also have growth ability. Examples of the pluripotent stem cells include, but are not limited to, embryonic stem (ES) cells, embryonic stem cells derived from a cloned embryo obtained by nuclear transfer ("ntES cells"), germline stem cells ("GS cells"), embryonic germ cells ("EG cells"), induced pluripotent stem (iPS) cells, and pluripotent cells derived from cultured fibroblasts and bone marrow stem cells (Muse cells). The pluripotent stem cells are preferably ES cells, ntES cells or iPS cells.

(A) Embryonic Stem Cells

ES cells are stem cells established from the inner cell mass of an early embryo (for example, blastocyst) of a mammal such as human or mouse, which cells have pluripotency and growth ability by self-renewal.

ES cells are embryo-derived stem cells originated from the inner cell mass of a blastocyst, which is the embryo formed following the 8-cell stage and the morula stage of a fertilized egg. ES cells have ability to differentiate into any cells constituting an adult, that is, the so-called pluripotency of differentiation, and growth ability by self-renewal. ES cells were discovered in mouse in 1981 (M. J. Evans and M. H. Kaufman (1981), Nature 292:154-156), and this was followed by establishment of ES cell lines of primates such as human and monkey (J. A. Thomson et al. (1998), Science 282:1145-1147; J. A. Thomson et al. (1995), Proc. Natl. Acad. Sci. USA, 92:7844-7848; J. A. Thomson et al. (1996), Biol. Reprod., 55:254-259; J. A. Thomson and V. S. Marshall (1998), Curr. Top. Dev. Biol., 38:133-165).

ES cells can be established by removing the inner cell mass from the blastocyst of a fertilized egg of a subject animal, followed by culturing the inner cell mass on feeder fibroblasts. The cells can be maintained by subculture using a medium supplemented with a substance(s) such as leukemia inhibitory factor (LIF) and/or basic fibroblast growth factor (bFGF). Methods of establishment and maintenance of human and monkey ES cells are described in, for example, U.S. Pat. No. 5,843,780 B; Thomson J A, et al. (1995), Proc Natl. Acad. Sci. USA. 92:7844-7848; Thomson J A, et al. (1998), Science. 282:1145-1147; H. Suemori et al. (2006), Biochem. Biophys. Res. Commun., 345:926-932; M. Ueno et al. (2006), Proc. Natl. Acad. Sci. USA, 103: 9554-9559; H. Suemori et al. (2001), Dev. Dyn., 222:273-279; H. Kawasaki et al. (2002), Proc. Natl. Acad. Sci. USA, 99:1580-1585; and Klimanskaya I, et al. (2006), Nature. 444:481-485.

In terms of the medium for preparation of ES cells, human ES cells can be maintained, for example, using DMEM/F-12 medium supplemented with 0.1 mM 2-mercaptoethanol, 0.1 mM non-essential amino acids, 2 mM L-glutamic acid, 20% KSR, and 4 ng/ml bFGF at 37° C. under a moist atmosphere of 2% $CO_2$/98% air (O. Fumitaka et al. (2008), Nat. Biotechnol., 26:215-224). ES cells need to be subcultured every 3 to 4 days, and the subculture can be carried out using 0.25% trypsin and 0.1 mg/ml collagenase IV in PBS supplemented with 1 mM $CaCl_2$ and 20% KSR.

Selection of ES cells can be generally carried out by the Real-Time PCR method using as an index/indices expression of a gene marker(s) such as alkaline phosphatase, Oct-3/4, and/or Nanog. In particular, for selection of human ES cells, expression of a gene marker(s) such as OCT-3/4, NANOG, and/or ECAD can be used as an index/indices (E. Kroon et al. (2008), Nat. Biotechnol., 26:443-452).

In terms of human ES cell lines, for example, WA01(H1) and WA09(H9) can be obtained from WiCell Research Institute, and KhES-1, KhES-2, and KhES-3 can be obtained from Institute for Frontier Medical Sciences, Kyoto University (Kyoto, Japan).

(B) Germline Stem Cells

Germline stem cells are pluripotent stem cells derived from testis, and play a role as the origin for spermatogenesis. Similarly to ES cells, these cells can be induced to differentiate into various series of cells, and, for example, have a property to enable preparation of a chimeric mouse by transplantation of the cells to a mouse blastocyst (M. Kanatsu-Shinohara et al. (2003) Biol. Reprod., 69:612-616; K. Shinohara et al. (2004), Cell, 119:1001-1012). Germline stem cells are capable of self-renewal in a medium containing glial cell line-derived neurotrophic factor (GDNF), and, by repeating subculture under the same culture conditions as those for ES cells, germline stem cells can be obtained (Masanori Takehashi et al. (2008), Experimental Medicine, 26(5) (extra edition):41-46, Yodosha (Tokyo, Japan)).

(C) Embryonic Germ Cells

Embryonic germ cells are established from fetal primordial germ cells and have pluripotency similarly to ES cells. They can be established by culturing primordial germ cells in the presence of substances such as LIF, bFGF, and stem cell factor (Y. Matsui et al. (1992), Cell, 70:841-847; J. L. Resnick et al. (1992), Nature, 359:550-551).

(D) Induced Pluripotent Stem Cells

Induced pluripotent stem (iPS) cells can be prepared by introducing specific reprogramming factors to somatic cells, which reprogramming factors are in the form of DNA or protein. iPS cells are somatic cell-derived artificial stem cells having properties almost equivalent to those of ES cells, such as pluripotency of differentiation and growth ability by self-renewal (K. Takahashi and S. Yamanaka (2006) Cell, 126:663-676; K. Takahashi et al. (2007), Cell, 131:861-872; J. Yu et al. (2007), Science, 318:1917-1920; Nakagawa, M. et al., Nat. Biotechnol. 26:101-106 (2008); WO 2007/069666). The reprogramming factors may be constituted by genes or gene products thereof, or non-coding RNAs, which are expressed specifically in ES cells; or genes or gene products thereof, non-coding RNAs, or low molecular weight compounds, which play important roles in maintenance of the undifferentiated state of ES cells. Examples of the genes included in the reprogramming factors include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3, and Glis1, and these reprogramming factors may be used either individually or as a combination of two or more of these. Examples of the combinations of the reprogramming factors include those described in WO 2007/069666; WO 2008/118820; WO 2009/007852; WO 2009/032194; WO 2009/058413; WO 2009/057831; WO 2009/075119; WO 2009/079007; WO 2009/091659; WO 2009/101084; WO 2009/101407; WO 2009/102983; WO 2009/114949; WO 2009/117439; WO 2009/126250; WO 2009/126251; WO 2009/126655; WO 2009/157593; WO 2010/009015; WO 2010/033906; WO 2010/033920; WO 2010/042800; WO 2010/050626; WO 2010/056831; WO 2010/068955; WO 2010/098419; WO 2010/102267; WO 2010/111409; WO 2010/111422; WO 2010/115050; WO 2010/124290; WO 2010/147395; WO 2010/147612; Huangfu D, et al. (2008), Nat. Biotechnol., 26: 795-797; Shi Y, et al. (2008), Cell Stem Cell, 2: 525-528; Eminli S, et al. (2008), Stem Cells. 26:2467-2474; Huangfu D, et al. (2008), Nat Biotechnol. 26:1269-1275; Shi Y, et al. (2008), Cell Stem Cell, 3, 568-574; Zhao Y, et al. (2008), Cell Stem Cell, 3:475-479; Marson A, (2008), Cell Stem Cell, 3, 132-135; Feng B, et al. (2009), Nat Cell Biol. 11:197-203; R. L. Judson et al., (2009), Nat. Biotech., 27:459-461; Lyssiotis C A, et al. (2009), Proc Natl Acad Sci USA. 106:8912-8917; Kim J B, et al. (2009), Nature. 461:649-643; Ichida J K, et al. (2009), Cell Stem Cell. 5:491-503; Heng J C, et al. (2010), Cell Stem Cell. 6:167-74; Han J, et al. (2010), Nature. 463:1096-100; Mali P, et al. (2010), Stem Cells. 28:713-720; and Maekawa M, et al. (2011), Nature. 474: 225-9.

Examples of the above-described reprogramming factors also include histone deacetylase (HDAC) inhibitors [for example, low molecular weight inhibitors such as valproic acid (VPA), trichostatin A, sodium butyrate, MC 1293, and M344; and nucleic acid-type expression inhibitors such as siRNAs and shRNAs against HDAC (e.g., HDAC1 siRNA Smartpool (Millipore) and HuSH 29 mer shRNA Constructs against HDAC1 (OriGene))], MEK inhibitors (for example, PD184352, PD98059, U0126, SL327, and PD0325901), glycogen synthase kinase-3 inhibitors (for example, Bio and CHIR99021), DNA methyltransferase inhibitors (for example, 5'-azacytidine), histone methyltransferase inhibitors (for example, low molecular weight inhibitors such as BIX-01294; and nucleic acid-type expression inhibitors such as siRNAs and shRNAs against Suv39h1, Suv39h2, SetDB1, and G9a), L-channel calcium agonists (for example, Bayk8644), butyric acid, TGFβ inhibitors or ALK5 inhibitors (for example, LY364947, SB431542, 616453, and A83-01), p53 inhibitors (for example, siRNAs and shRNAs against p53), ARID3A inhibitors (for example, siRNAs and shRNAs against ARID3A), miRNAs such as miR-291-3p, miR-294, miR-295, and mir-302, Wnt Signaling (for example, soluble Wnt3a), neuropeptide Y, prostaglandins (for example, prostaglandin E2 and prostaglandin J2), hTERT, SV40LT, UTF1, IRX6, GLIS1, PITX2, and DMRTB1, which are employed for enhancing the establishment efficiency, and, in the present description, these factors employed for the purpose of enhancement of the establishment efficiency are not particularly distinguished from reprogramming factors.

In cases where the reprogramming factors are in the form of protein, the reprogramming factors may be introduced into somatic cells by a method such as lipofection, fusion with a cell membrane-permeable peptide (e.g., HIV-derived TAT or polyarginine), or microinjection.

In cases where the reprogramming factors are in the form of DNA, the reprogramming factors may be introduced into somatic cells by a method such as use of a vector including virus, plasmid, and artificial chromosome vectors; lipofection; use of liposome; or microinjection. Examples of the virus vectors include retrovirus vectors, lentivirus vectors (these are described in Cell, 126, pp. 663-676, 2006; Cell, 131, pp. 861-872, 2007; and Science, 318, pp. 1917-1920, 2007), adenovirus vectors (Science, 322, 945-949, 2008), adeno-associated virus vectors, and Sendai virus vectors (WO 2010/008054). Examples of the artificial chromosome vectors include human artificial chromosomes (HACs), yeast artificial chromosomes (YACs), and bacterial artificial chromosomes (BACs and PACs). Examples of the plasmids which may be used include plasmids for mammalian cells (Science, 322:949-953, 2008). The vectors may contain a regulatory sequence(s) such as a promoter, enhancer, ribosome binding sequence, terminator, and/or polyadenylation site for allowing expression of the nuclear reprogramming substances; and, as required, a sequence of a selection marker such as a drug resistance gene (e.g., kanamycin-resistant gene, ampicillin-resistant gene, or puromycin-resistant gene), thymidine kinase gene, or diphtheria toxin gene; a gene sequence of a reporter such as the green-fluorescent protein (GFP), β-glucuronidase (GUS), or FLAG; and/or the like. Further, in order to remove, after introduction of the above vector into somatic cells, the genes encoding the reprogramming factors, or both the promoters and the genes encoding the reprogramming factors linked thereto, the vector may have LoxP sequences upstream and downstream of these sequences.

In cases where the reprogramming factors are in the form of RNA, each reprogramming factor may be introduced into somatic cells by a method such as lipofection or microinjection, and RNA in which 5-methylcytidine and pseudouridine (TriLink Biotechnologies) are incorporated may be used in order to suppress degradation (Warren L, (2010) Cell Stem Cell. 7:618-630).

Examples of the medium for induction of the iPS cells include DMEM, DMEM/F12, and DME media supplemented with 10 to 15% FBS (these media may further contain LIF, penicillin/streptomycin, puromycin, L-glutamine, non-essential amino acids, 2-mercaptoethanol, and/or the like, as appropriate); and commercially available media [for example, a medium for culturing mouse ES cells (TX-WES medium, Thromb-X), medium for culturing primate ES cells (medium for primate ES/iPS cells, Repro-CELL), and serum-free medium (mTeSR, Stemcell Technology)].

Examples of the culture method include a method wherein somatic cells and reprogramming factors are brought into contact with each other at 37° C. in the presence of 5% $CO_2$ on DMEM or DMEM/F12 medium supplemented with 10% FBS, and the cells are cultured for about 4 to 7 days, followed by plating the cells on feeder cells (e.g., mitomycin C-treated STO cells or SNL cells) and starting culture in a bFGF-containing medium for culturing primate ES cells about 10 days after the contact between the somatic cells and the reprogramming factors, thereby allowing iPS-like colonies to appear about 30 to about 45 days after the contact, or later.

Alternatively, the cells may be cultured at 37° C. in the presence of 5% $CO_2$ on feeder cells (e.g., mitomycin C-treated STO cells or SNL cells) in DMEM medium supplemented with 10% FBS (this medium may further contain LIF, penicillin/streptomycin, puromycin, L-glutamine, non-essential amino acids, 2-mercaptoethanol, and/or the like, as appropriate) for about 25 to about 30 days or longer, to allow ES-like colonies to appear. Preferred examples of the culture method include a method wherein the somatic cells themselves to be reprogrammed are used instead of the feeder cells (Takahashi K, et al. (2009), PLoS One. 4:e8067 or WO 2010/137746), and a method wherein an extracellular matrix (e.g., Laminin-5 (WO 2009/123349) or Matrigel (BD)) is used instead.

Other examples of the culture method include a method wherein culture is carried out using a serum-free medium (Sun N, et al. (2009), Proc Natl Acad Sci USA. 106:15720-15725). Further, in order to enhance the establishment efficiency, iPS cells may be established under low oxygen conditions (at an oxygen concentration of 0.1% to 15%) (Yoshida Y, et al. (2009), Cell Stem Cell. 5:237-241 or WO 2010/013845).

During the culture, the medium is replaced with a fresh medium once every day from Day 2 of the culture. The number of the somatic cells used for nuclear reprogramming is not restricted, and usually within the range of about $5\times10^3$ to about $5\times10^6$ cells per 100-cm$^2$ area on the culture dish.

iPS cells can be selected based on the shape of each formed colony. In cases where a drug resistance gene expressed in conjunction with a gene that is expressed upon reprogramming of a somatic cell (e.g., Oct3/4 or Nanog) is introduced as a marker gene, established iPS cells can be selected by culturing the cells in a medium containing the corresponding drug (selection medium). iPS cells can be selected by observation under a fluorescence microscope in cases where the marker gene is the gene of a fluorescent protein; by adding a luminescent substrate in cases where the marker gene is the gene of luciferase; or by adding a coloring substrate in cases where the marker gene is the gene of a coloring enzyme.

The term "somatic cells" used in the present description means any animal cells (preferably cells of mammals including human) excluding germ-line cells and totipotent cells such as eggs, oocytes, and ES cells. Examples of the somatic cells include, but are not limited to, any of fetal somatic cells, neonatal somatic cells, and mature, healthy and diseased somatic cells, as well as any of primary cultured cells, subcultured cells, and established cell lines. Specific examples of the somatic cells include (1) tissue stem cells (somatic stem cells) such as neural stem cells, hematopoietic stem cells, mesenchymal stem cells, and dental pulp stem cells; (2) tissue progenitor cells; and (3) differentiated cells such as lymphocytes, epithelial cells, endothelial cells, muscle cells, fibroblasts (skin cells and the like), hair cells, hepatic cells, gastric mucosal cells, enterocytes, spleen cells, pancreatic cells (pancreatic exocrine cells and the like), brain cells, lung cells, kidney cells, and adipocytes.

In cases where iPS cells are used as a material for the cells to be transplanted, somatic cells whose HLA genotype is the same or substantially the same as that of the individual to which the cells are to be transplanted are preferably used in view of prevention of the rejection reaction. The term "substantially the same" herein means that the HLA genotype is matching to an extent at which the immune reaction against the transplanted cells can be suppressed with an immunosuppressive agent. For example, the somatic cells have matched HLA types at 3 loci HLA-A, HLA-B, and HLA-DR, or at the 4 loci further including HLA-C.

(E) ES Cells Derived from Cloned Embryo Obtained by Nuclear Transfer ntES cells are ES cells derived from a cloned embryo prepared by the nuclear transfer technique, and have almost the same properties as those of ES cells derived from fertilized eggs (T. Wakayama et al. (2001), Science, 292: 740-743; S. Wakayama et al. (2005), Biol. Reprod., 72:932-936; J. Byrne et al. (2007), Nature, 450:497-502). That is, an ntES (nuclear transfer ES) cell is an ES cell established from the inner cell mass of a blastocyst derived from a cloned embryo obtained by replacement of the nucleus of an unfertilized egg with the nucleus of a somatic cell. For preparation of an ntES cell, the combination of the nuclear transfer technique (J. B. Cibelli et al. (1998), Nature Biotechnol., 16:642-646) and the ES cell preparation technique (described above) is employed (Sayaka Wakayama et al. (2008), Experimental Medicine 26(5) (extra edition), pp. 47-52). In nuclear transfer, reprogramming can be achieved by injecting the nucleus of a somatic cell into a mammalian enucleated unfertilized egg and culturing the resultant for several hours.

(F) Multilineage-Differentiating Stress Enduring Cells (Muse Cells)

Muse cells are pluripotent stem cells produced by the method described in WO 2011/007900. More specifically, Muse cells are cells having pluripotency obtained by subjecting fibroblasts or bone marrow stromal cells to trypsin treatment for a long period, preferably to trypsin treatment for 8 hours or 16 hours, followed by suspension culture of the treated cells. Muse cells are positive for SSEA-3 and CD105.

<Dopaminergic Neuron Progenitor Cells>

In the present invention, "dopaminergic neuron progenitor cells" also includes dopaminergic neural cells, dopaminergic neurons, and the like. The dopaminergic neuron progenitor cells may be a cell population containing other types of cells. The cell population is preferably a cell population which does not contain a serotonin neural cell. The dopaminergic neuron progenitor cells are preferably a cell population containing Foxa2Nurr1- and/or TH-positive cells. In the present invention, examples of human Foxa2 include the polynucleotides of NCBI accession Nos. NM_021784 and NM_153675, and proteins encoded by these polynucleotides. In the present invention, examples of human Nurr1 include the polynucleotide of NCBI accession No. NM_006186, and proteins encoded by this polynucleotide. In the present invention, examples of human TH include the polynucleotides of NCBI accession Nos. NM_000360, NM_199292, and NM_199293, and proteins encoded by these polynucleotides.

<Extracellular Matrix>

In the present invention, the extracellular matrix is a supramolecular structure present outside the cell, and may be either a naturally-occurring substance or an artificial (recombinant) substance. Examples of the extracellular matrix include substances such as collagen, proteoglycan, fibronectin, hyaluronic acid, tenascin, entactin, elastin, fibrillin, and laminin, and fragments thereof. Two or more of these extracellular matrices may be used in combination. For example, the extracellular matrix may be a product prepared from cells, such as BD Matrigel (trademark). The extracellular matrix is preferably laminin or a fragment thereof. The laminin in the present invention is not limited as long as it has a heterotrimeric structure composed of an α-chain, a β-chain, and a γ-chain. Examples of the α-chain include α1, α2, α3, α4, and α5; examples of the β-chain include β1, β2, and β3; and examples of the γ-chain include γ1, γ2, and γ3. The laminin is more preferably laminin 511, which is composed of α5, β1, and γ1. The laminin in the present invention may also be a fragment of laminin, and the fragment is not limited as long as it has an integrin-binding activity. For example, the fragment of laminin may be E8 fragment, which is a fragment obtained by digestion with elastase. Accordingly, an example of the laminin in the present invention is laminin 511E8 (preferably human laminin 511E8), which is described in WO 2011/043405.

<BMP Inhibitor>

Examples of the BMP inhibitor in the present invention include protein-based inhibitors such as Chordin, Noggin and Follistatin; Dorsomorphin (that is, 6-[4-(2-piperidin-1-yl-ethoxy)phenyl]-3-pyridin-4-yl-pyrazolo[1,5-a]pyrimidine) and its derivatives (P. B. Yu et al. (2007), Circulation, 116:II_60; P. B. Yu et al. (2008), Nat. Chem. Biol., 4:33-41; J. Hao et al. (2008), PLoS ONE, 3(8):e2904); and LDN193189 (that is, 4-(6-(4-(piperazin-1-yl)phenyl)pyrazolo[1,5-a]pyrimidin-3-yl)quinoline). Dorsomorphin and LDN193189 are commercially available, and can be obtained from Sigma-Aldrich and Stemgent, respectively. The BMP inhibitor to be used in the present invention may be preferably LDN193189.

The concentration of LDN193189 in the medium is not limited as long as BMP can be inhibited at the concentration. Examples of the concentration of LDN193189 include, but are not limited to, 1 nM, 10 nM, 50 nM, 100 nM, 500 nM, 750 nM, 1 μM, 2 μM, 3 μM, 4 μM, 5 μM, 6 μM, 7 μM 20 μM, 25 μM, 30 μM, 40 μM, and 50 μM. The concentration is preferably 100 nM.

<TGFβ Inhibitor>

The TGFβ inhibitor in the present invention is a substance which inhibits signal transduction that proceeds from binding of TGFβ to its receptor to SMAD. Examples of the TGFβ inhibitor include substances that inhibit binding to the ALK family, which is a receptor, and substances that inhibit phosphorylation of SMAD by the ALK family. Specific examples of the TGFβ inhibitor include Lefty-1 (e.g., NCBI Accession Nos. NM_010094 (mouse) and NM_020997 (human)); SB431542 and SB202190 (these are described in R. K. Lindemann et al., Mol. Cancer, 2003, 2:20); SB505124 (GlaxoSmithKline); NPC30345, SD093, SD908, and SD208 (Scios); LY2109761, LY364947, and LY580276 (Lilly Research Laboratories); A83-01 (WO 2009146408); and derivatives thereof. The TGFβ inhibitor to be used in the present invention may be preferably A83-01.

The concentration of A83-01 in the medium is not limited as long as ALK5 can be inhibited at the concentration. Examples of the concentration of A83-01 include, but are not limited to, 1 nM, 10 nM, 50 nM, 100 nM, 500 nM, 750 nM, 1 μM, 2 μM, 3 μM, 4 μM, 5 μM, 6 μM, 7 μM, 8 μM, 9 μM, 10 μM, 15 μM, 20 μM, 25 μM, 30 μM, 40 μM, and 50 μM. The concentration is preferably 500 nM to 5 μM, more preferably 500 nM.

<SHH Signal-Stimulating Agent>

The SHH (Sonic hedgehog) signal-stimulating agent in the present invention is defined as a substance that causes disinhibition of Smoothened (Smo) due to binding of SHH to its receptor, Patched (Ptch1), and also causes activation of Gli2, which follows the disinhibition. Examples of the SHH signal-stimulating agent include SHH, Hh-Ag1.5 (Li, X., et al., Nature Biotechnology, 23, 215-221 (2005)), Smoothened Agonist, SAG (N-Methyl-N'-(3-pyridinylbenzyl)-N'-(3-chlorobenzo[b]thiophene-2-carbonyl)-1,4-diaminocyclohexane), 20a-hydroxycholesterol, purmorphamine, and derivatives thereof (Stanton B Z, Peng L F., Mol Biosyst. 6:44-54, 2010). The SHH signal-stimulating agent to be used in the present invention may be preferably purmorphamine.

The concentration of purmorphamine in the medium is not limited as long as Gli2 can be activated at the concentration. Examples of the concentration of purmorphamine include, but are not limited to, 1 nM, 10 nM, 50 nM, 100 nM, 500 nM, 750 nM, 1 μM, 2 μM, 3 μM, 4 μM, 5 μM, 6 μM, 7 μM, 8 μM, 9 μM, 10 μM, 15 μM, 20 μM, 25 μM, 30 μM, 40 μM, and 50 μM. The concentration is preferably 2 μM.

<GSK3β Inhibitor>

In the present invention, GSK3β inhibitor is defined as a substance which inhibits kinase activity (for example, ability to phosphorylate β-catenin) of GSK-3β protein. A number of GSK3β inhibitors are known, and examples of the GSK3β inhibitors include BIO (another name, GSK-3β inhibitor IX; 6-bromoindirubin-3'-oxime), which is an indirubin derivative; SB216763 (3-(2,4-dichlorophenyl)-4-(1-methyl-1H-indol-3-yl)-1H-pyrrole-2,5-dione), which is a maleimide derivative; GSK-3β inhibitor VII (4-dibromoacetophenone), which is a phenyl α-bromomethyl ketone compound; L803-mts (another name, GSK-3β peptide inhibitor; Myr-N-GKEAPPAPPQpSP-NH2 (SEQ ID NO:1)), which is a cell membrane-permeable phosphorylated peptide; and CHIR99021 (6-[2-[4-(2,4-dichlorophenyl)-5-(4-methyl-1H-imidazol-2-yl)pyrimidin-2-ylamino]ethylamino]pyridine-3-carbonitrile), which has high selectivity. These compounds are commercially available from, for example, Calbiochem and Biomol, and can be easily employed. The compounds may also be obtained from other sources, or may be prepared. The GSK3β inhibitor to be used in the present invention may be preferably CHIR99021.

Examples of the concentration of CHIR99021 in the medium include, but are not limited to, 1 nM, 10 nM, 50 nM, 100 nM, 500 nM, 750 nM, 1 μM, 2 μM, 3 μM, 4 μM, 5 μM, 6 μM, 7 μM, 8 μM, 9 μM, 10 μM, 15 μM, 20 μM, 25 μM, 30 μM, 40 μM, and 50 μM. The concentration is preferably 1 μM.

<FGF8>

In the present invention, the FGF8 is not limited, and, in cases of human FGF8, examples of the FGF8 include the following four splicing forms: FGF8a, FGF8b, FGF8e, and FGF8f. The FGF8 in the present invention is more preferably FGF8b. FGF8 is commercially available from, for example, Wako Pure Chemical Industries, Ltd. and R&D Systems, Inc., and can be easily employed. The FGF8 may also be obtained by forced expression in cells by a method known to those skilled in the art.

Examples of the concentration of FGF8 in the medium include, but are not limited to, 1 ng/mL, 5 ng/mL, 10 ng/mL, 50 ng/mL, 100 ng/mL, 150 ng/mL, 200 ng/mL, 250 ng/mL, 500 ng/mL, 1000 ng/mL, 2000 ng/mL, and 5000 ng/mL. The concentration is preferably 100 ng/mL.

<Method for Selecting Cells>

In the present invention, the selection of Corin-positive cells and/or Lrtm1-positive cells from a cell population may be carried out using a substance(s) that specifically bind(s) to Corin and/or Lrtm1. As a substance that specifically binds to Corin or Lrtm1, an antibody or an aptamer may be used. The substance is preferably an antibody or an antigen-binding fragment thereof.

In the present invention, the antibody may be either a polyclonal or monoclonal antibody. These antibodies can be prepared using techniques well known to those skilled in the art (Current protocols in Molecular Biology edit. Ausubel et al. (1987) Publish. John Wiley and Sons. Sections 11.12-11.13). More specifically, in cases where the antibody is a polyclonal antibody, the polyclonal antibody can be obtained by allowing E. coli, a mammalian cell line, or the like to express a protein encoded by Corin or Lrtm1, or an oligopeptide or a glycolipid having a partial amino acid sequence thereof, according to a conventional method, and purifying the resulting expression product, followed by immunization of a non-human mammal such as a rabbit therewith and isolating the polyclonal antibody from the serum of the immunized animal according to a conventional method. In cases where the antibody is a monoclonal antibody, the monoclonal antibody can be obtained from hybridoma cells prepared by cell fusion of spleen cells obtained from the above-described immunized non-human mammal with myeloma cells (Current protocols in Molecular Biology edit. Ausubel et al. (1987) Publish. John Wiley and Sons. Sections 11.4-11.11). Examples of the antigen-binding fragment of the antibody include fragments of the antibody (e.g., Fab fragment) and synthetic antibody fragments (e.g., single-chain Fv fragment "ScFv"). Antibody fragments such as the Fab and F(ab)$_2$ fragments can also be prepared by well known methods in genetic engineering. For example, an antibody against Corin can be obtained by the preparation methods described in WO 2004/065599 and WO 2006/009241, and an antibody against Lrtm1 can be obtained by the preparation method described in WO 2013/015457.

A sequence of human Corin can be obtained from NCBI accession No. NM_006587. Similarly, a sequence of human Lrtm1 can be obtained from NM_020678.

For the purpose of recognition or separation of cells expressing Corin or Lrtm1, the binding substance may be bound or conjugated, for example, to a detectable substance such as a fluorescent label, radioactive label, chemiluminescent label, enzyme, biotin, or streptavidin, or to a substance that allows isolation/extraction of the cells, such as protein A, protein G, beads, or magnetic beads.

Alternatively, the binding substance may be indirectly labeled. The labeling may be carried out by various methods known to those skilled in the art, and examples of the methods include a method in which a preliminarily labeled antibody (secondary antibody) that specifically binds to the antibody is used.

Examples of the method for detecting the dopaminergic neuron progenitor cells include use of a flow cytometer, protein chip, or the like.

Examples of the method for extracting the dopaminergic neuron progenitor cells include a method in which the binding substance is conjugated to particles to cause precipitation of the resulting conjugate, a method in which the cells are sorted using magnetic beads having magnetism (e.g., MACS), a method in which a fluorescent label and a cell sorter are used, and a method in which a carrier (e.g., cell-concentrating column) to which an antibody or the like is immobilized is used.

In the present invention, the aptamer which specifically binds to Corin or Lrtm1 can be prepared using a technique well known to those skilled in the art (SELEX (systematic evolution of ligand by exponential enrichment) method: Ellington, A. D. & Szostak, J. W. (1990) Nature, 346, 818-822; Tuerk, C. & Gold, L. (1990) Science, 249, 505-510).

<Neurotrophic Factor>

In the present invention, the neurotrophic factor means a ligand for a membrane receptor playing an important role in survival and maintenance of the function of motor neurons. Examples of the neurotrophic factor include Nerve Growth Factor (NGF), Brain-derived Neurotrophic Factor (BDNF), Neurotrophin 3 (NT-3), Neurotrophin 4/5 (NT-4/5), Neurotrophin 6 (NT-6), basic FGF, acidic FGF, FGF-5, Epidermal Growth Factor (EGF), Hepatocyte Growth Factor (HGF), Insulin, Insulin Like Growth Factor 1 (IGF 1), Insulin Like Growth Factor 2 (IGF 2), Glia cell line-derived Neurotrophic Factor (GDNF), TGF-b2, TGF-b3, Interleukin 6 (IL-6), Ciliary Neurotrophic Factor (CNTF), and LIF. In the present invention, the neurotrophic factor is preferably a factor selected from the group consisting of GDNF and BDNF. Neurotrophic factors are commercially available from, for example, Wako Pure Chemical Industries, Ltd. and R&D Systems, Inc., and can be easily employed. The neurotrophic factor may also be obtained by forced expression in cells by a method known to those skilled in the art.

Examples of the concentration of GDNF1 in the medium include, but are not limited to, 0.1 ng/mL, 0.5 ng/mL, 1 ng/mL, 5 ng/mL, 10 ng/mL, 15 ng/mL, 20 ng/mL, 25 ng/mL, 30 ng/mL, 40 ng/mL, 50 ng/mL, 100 ng/mL, 200 ng/mL, and 500 ng/mL. The concentration is preferably 10 ng/mL.

Examples of the concentration of BDNF1 in the medium include, but are not limited to, 0.1 ng/mL, 0.5 ng/mL, 1 ng/mL, 5 ng/mL, 10 ng/mL, 15 ng/mL, 20 ng/mL, 25 ng/mL, 30 ng/mL, 40 ng/mL, 50 ng/mL, 100 ng/mL, 200 ng/mL, and 500 ng/mL. The concentration is preferably 20 ng/mL.

<Step (i)>

In the present invention, the Step (i) is preferably carried out by the following multistep process comprising the steps of:

(a) performing adherent culture of pluripotent stem cells on an extracellular matrix in a medium containing BMP inhibitor and a TGFβ inhibitor;

(b) performing adherent culture of the cells obtained in Step (a) on an extracellular matrix in a medium containing BMP inhibitor, TGFβ inhibitor, SHH signal-stimulating agent, and FGF8;

(c) performing adherent culture of the cells obtained in Step (b) on an extracellular matrix in a medium containing BMP inhibitor, TGFβ inhibitor, SHH signal-stimulating agent, FGF8, and GSK3β inhibitor; and (d) performing adherent culture of the cells obtained in Step (c) on an extracellular matrix in a medium containing BMP inhibitor and GSK3β inhibitor.

In the present invention, the medium to be used in Step (i) may be prepared using a medium for animal cell culture as a basal medium. Examples of the basal medium include Glasgow's Minimal Essential Medium (GMEM), IMDM, Medium 199, Eagle's Minimum Essential Medium (EMEM), aMEM, Dulbecco's modified Eagle's Medium (DMEM), Ham's F12 medium, RPMI 1640 medium, Fischer's medium, Neurobasal Medium (Life Technologies), and mixtures of two or more of these media. The medium is preferably GMEM. The medium may contain serum, or may be serum-free. If necessary, the medium may contain one or more of serum replacements such as albumin, transferrin, Knockout Serum Replacement (KSR) (serum replacement for FBS in ES cell culture), N2 supplement (Invitrogen), B27 supplement (Invitrogen), fatty acids, insulin, collagen precursor, trace elements, 2-mercaptoethanol, and 3'-thiolglycerol, and may also contain one or more of substances such as lipids, amino acids, L-glutamine, Glutamax (Invitrogen), non-essential amino acids, vitamins, growth factors, low-molecular-weight compounds, antibiotics, antioxidants, pyruvic acid, buffers, and inorganic salts. A preferred medium is GMEM, which contains KSR, 2-mercaptoethanol, non-essential amino acids, and pyruvic acid. The medium may be supplemented, if necessary, with a reagent(s) selected from the group consisting of BMP inhibitor, TGFβ inhibitor, SHH signal-stimulating agent, FGF8, and GSK3β inhibitor, and used for the culture.

The "adherent culture on an extracellular matrix" in Step (i) may be carried out by culturing the cells using a culture vessel coated with an extracellular matrix. The coating treatment may be carried out by placing a solution containing the extracellular matrix in the culture vessel, and then removing the solution as appropriate.

In terms of the culture conditions, the culture temperature is not limited, and may be about 30 to 40° C., preferably about 37° C. The culture is carried out under an atmosphere of $CO_2$-containing air, wherein the $CO_2$ concentration is preferably about 2 to 5%.

The culture period is not limited as long as Corin- and/or Lrtm1-positive cells appear during the period. Step (i) is preferably carried out for at least 10 days. The period of Step (i) is more preferably 12 days to 21 days, still more preferably 12 days to 14 days.

In Step (i), examples of the period of Step (a) include not less than 1 day, not less than 2 days, not less than 3 days, not less than 4 days, not less than 5 days, not less than 6 days, not less than 7 days, and periods longer than these. The period of Step (a) is preferably 1 day. Similarly, examples of the period of Step (b) include not less than 1 day, not less than 2 days, not less than 3 days, not less than 4 days, not less than 5 days, not less than 6 days, not less than 7 days, and periods longer than these. The period of Step (b) is preferably 2 days. Similarly, examples of the period of Step (c) include not less than 1 day, not less than 2 days, not less than 3 days, not less than 4 days, not less than 5 days, not less than 6 days, not less than 7 days, and periods longer than these. The period of Step (c) is preferably 4 days. Similarly, examples of the period of Step (d) include not less than 1 day, not less than 2 days, not less than 3 days, not less than 4 days, not less than 5 days, not less than 6 days, not less than 7 days, and periods longer than these. The period of Step (d) is preferably not less than 5 days.

The pluripotent stem cells may be dissociated. Examples of the method for dissociating the pluripotent stem cells include a method in which the cells are mechanically dissociated, and a method in which a dissociation solution having protease activity and collagenase activity (e.g., Accutase (trademark) or Accumax (trademark)) or a dissociation solution having only collagenase activity is used. The method is preferably a method in which human pluripotent stem cells are dissociated using trypsin or an alternative thereto (e.g., TrypLE CTS (Life Technologies)). In cases where the cells are dissociated, it is preferred to add a ROCK inhibitor as appropriate after the dissociation, followed by performing culture of the dissociated cells. In cases where a ROCK inhibitor is added, the culture in the presence of the ROCK inhibitor may be carried out for at least one day. The culture is more preferably carried out for one day.

<ROCK Inhibitor>

In the present invention, the ROCK inhibitor is not limited as long as the ROCK inhibitor can suppress the function of Rho kinase (ROCK). Examples of the ROCK inhibitor include Y-27632 (see, for example, Ishizaki et al., Mol. Pharmacol. 57, 976-983 (2000) or Narumiya et al., Methods Enzymol. 325, 273-284 (2000)), Fasudil/HA1077 (see, for example, Uenata et al., Nature 389: 990-994 (1997)), H-1152 (see, for example, Sasaki et al., Pharmacol. Ther. 93: 225-232 (2002)), Wf-536 (see, for example, Nakajima et al., Cancer Chemother Pharmacol. 52(4): 319-324 (2003)), and derivatives thereof; antisense nucleic acids, RNA interference-inducing nucleic acids (e.g., siRNAs), and dominant negative mutants against ROCK, and expression vectors therefor. Other low-molecular-weight compounds are also known as ROCK inhibitors, and these compounds and derivatives thereof may also be used in the present invention (see, for example, US 20050209261 A, US 20050192304 A, US 20040014755 A, US 20040002508 A, US 20040002507 A, US 20030125344 A, US 20030087919 A, WO 2003/062227, WO 2003/059913, WO 2003/062225, WO 2002/076976, and WO 2004/039796). In the present invention, one or more ROCK inhibitors may be used. The ROCK inhibitor to be used in the present invention may be preferably Y-27632.

Examples of the concentration of Y-27632 include, but are not limited to, 100 nM, 500 nM, 750 nM, 1 μM, 2 μM, 3 μM, 4 μM, 5 μM, 6 μM, 7 μM, 8 μM, 9 μM, 10 μM, 15 μM, 20 μM, 25 μM, 30 μM, 40 μM, and 50 μM. The concentration of Y-27632 is preferably 10 μM.

<Step (ii)>

The step (ii) of collecting Corin- and/or Lrtm1-positive cells may be carried out based on the <Method for Selecting Cells> described above.

<Step (iii)>

The medium to be used in Step (iii) may be prepared using a medium for animal cell culture as a basal medium. Examples of the basal medium include Glasgow's Minimal Essential Medium(GMEM), IMDM, Medium 199, Eagle's Minimum Essential Medium (EMEM), αMEM, Dulbecco's modified Eagle's Medium (DMEM), Ham's F12 medium, RPMI 1640 medium, Fischer's medium, Neurobasal Medium (Life Technologies), and mixtures of two or more of these media. The medium is preferably Neurobasal Medium. The medium may contain serum, or may be serum-free. If necessary, the medium may contain one or more of serum replacements such as albumin, transferrin, Knockout Serum Replacement (KSR) (serum replacement for FBS in ES cell culture), N2 supplement (Invitrogen), B27 supplement (Invitrogen), fatty acids, insulin, collagen precursor, trace elements, 2-mercaptoethanol, and 3'-thiolglycerol, and may also contain one or more of substances such as lipids, amino acids, L-glutamine, Glutamax (Invitrogen), non-essential amino acids, vitamins, growth factors, low-molecular-weight compounds, antibiotics, antioxidants, pyruvic acid, buffers, inorganic salts, and nucleic acids (for example, dibutyryl cyclic AMP (dbcAMP)). A preferred medium is Neurobasal Medium supplemented with B27 supplement, ascorbic acid, and dbcAMP. The medium may be supplemented, if necessary, with a neurotrophic factor(s), and used for the culture.

The suspension culture in Step (iii) means culturing of the cells in a state where the cells are not adhering to the culture vessel. The culture vessel that may be used is not limited, and examples of the culture vessel include culture vessels that are not artificially treated for the purpose of enhancing adhesiveness to cells (for example, by coating treatment with an extracellular matrix or the like), and culture vessels that are artificially treated such that adhesion is suppressed (for example, by coating treatment with a polyhydroxyethylmethacrylate (poly-HEMA), a nonionic surface-active polyol (e.g., Pluronic F-127), or a phospholipid analogue (e.g., a water-soluble polymer containing 2-methacryloyloxyethyl phosphorylcholine as a constituent (Lipidure)).

In terms of the culture conditions, the culture temperature is not limited, and may be about 30 to 40° C., preferably about 37° C. The culture is carried out under an atmosphere of $CO_2$-containing air, wherein the $CO_2$ concentration is preferably about 2 to 5%.

The culture period is not limited as long as Nurr1- and/or Foxa2-positive cells appear during the period. Step (iii) is preferably carried out for at least 7 days. The period of Step (iii) is more preferably 7 days to 30 days, still more preferably 14 days to 21 days, or 14 days to 16 days. The period of Step (iii) is most preferably 16 days.

In cases where Step (iii) is carried out after Step (ii), it is preferred to add a ROCK inhibitor as appropriate to carry out the culture. In cases where a ROCK inhibitor is added, the culture in the presence of the ROCK inhibitor may be carried out for at least one day. The culture is more preferably carried out for one day.

<Therapeutic Agent for Parkinson's Disease>

The dopaminergic neuron progenitor cells obtained by the present invention may be prepared as a formulation for administration to patients with Parkinson's disease. The administration is carried out by suspending the obtained dopaminergic neuron progenitor cells in physiological saline or the like and transplanting the resulting suspension to the striate body area of the patient. Accordingly, the present invention provides a therapeutic agent for Parkinson's disease comprising dopaminergic neuron progenitor cells obtained from pluripotent stem cells by the above-described method.

In the present invention, the number of dopaminergic neuron progenitor cells contained in the therapeutic agent for Parkinson's disease is not limited as long as the transplant can survive after the administration. For example, not less than 15×10$^4$ cells may be contained. The number of the cells may be increased or decreased as appropriate depending on symptoms and/or the size of the body.

The transplantation of the dopaminergic neuron progenitor cells to the affected area may be carried out by a method described in, for example, Nature Neuroscience, 2, 1137 (1999) or N Engl J Med. 344: 710-9 (2001).

<Kit>

Other embodiments of the present invention include a kit for preparation of dopaminergic neuron progenitor cells from pluripotent stem cells. The kit comprises a medium, additives, culture vessel, and/or the like to be used for the above-described steps of preparation of dopaminergic neuron progenitor cells. For example, the kit may contain a reagent(s) selected from the group consisting of anti-Corin antibodies, anti-Lrtm1 antibodies, BMP inhibitor, TGFβ inhibitor, SHH signal-stimulating agent, FGF8, GSK3β inhibitor, extracellular matrices, and neurotrophic factors. The kit may further contain a document or an instruction in which a procedure for the production process is described.

The present invention is described below more concretely by way of Examples. However, needless to say, the present invention is not limited to these.

EXAMPLES

Example 1

Cells and Culture

Human ES cells (KhES-1) were obtained from Institute for Frontier Medical Sciences, Kyoto University (Suemori H, et al. Biochem Biophys Res Commun. 345:926-32, 2006). 404C2 and 836B3, which are human iPS cells produced by introducing Oct3/4, Sox2, Klf4, L-MYC, LIN28, and p53shRNA to human fibroblasts using an episomal vector, were received from Prof. Yamanaka at Kyoto University (Okita et al., Nat Methods. 8: 409-412, 2011).

The ES cells and the iPS cells were cultured by the method according to the method described in Miyazaki T et al. (Nat Commun. 3: 1236, 2012). Briefly, these cells were cultured in 6-well plates coated with Laminin 511E8.

Figure 2:
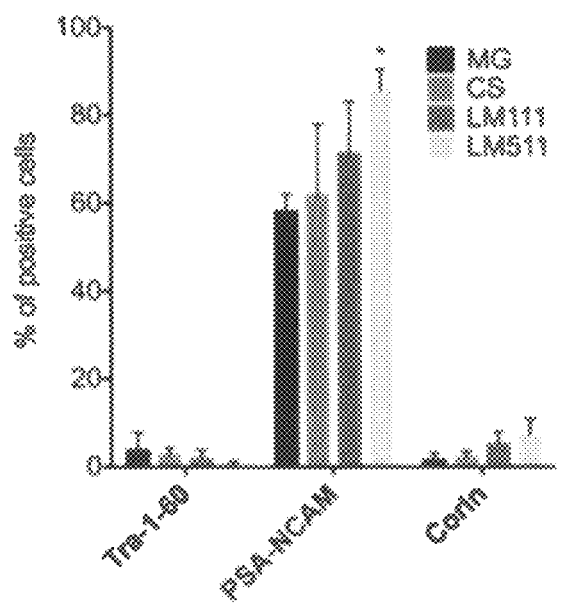
FIG. 2 shows a graph showing the proportion of Tra-1-60-positive cells, proportion of PSA-NCAM-positive cells, and proportion of Corin-positive cells on Day 12 when differentiation induction was carried out using MG (Matrigel), CS (CELLStart), LM111 (Laminin 111E8), or LM511 (Laminin 511E8) as a coating agent.

The thus obtained ES cells or iPS cells were dissociated using TrypLE CTS (Life Technologies), and transferred to a 6-well plate coated with Laminin 511E8 (iMatrix-511, Nippi) in an amount of 4×10$^4$ cells per well. The cells were then cultured by the above-described culture method for four days, and, after confirming confluence of the cells, the medium was replaced with Basal Medium A (GMEM (Invitrogen) supplemented with 8% KSR (Invitrogen), 1 mM sodium pyruvate (Invitrogen), 0.1 mM MEM non-essential amino acid (Invitrogen), and 0.1 mM 2-Mercaptoethanol (WAKO)) supplemented with 10 μM Y-27632 (WAKO), 0.1 μM LDN193189 (STEMGENT), and 0.5 μM A83-01 (WAKO). On the next day (Day 1), the medium was replaced with Basal Medium A supplemented with 0.1 μM LDN193189, 0.5 μM A83-01, 2 μM purmorphamine (WAKO), and 100 ng/mL FGF8 (WAKO). Two days later (Day 3), the medium was replaced with Basal Medium A supplemented with 0.1 μM LDN193189, 0.5 μM A83-01, 2 μM purmorphamine, 100 ng/mL FGF8, and 3 μM CHIR99021 (WAKO). Four days later (Day 7), the medium was replaced with Basal Medium A supplemented with 0.1 μM LDN193189 and 3 μM CHIR99021. Then, replacement of the medium was carried out once every day. The same experiment was carried out for 12 days except that Matrigel (BD), CELLstart (Invitrogen), or Laminin 111E8 was used instead of the coating agent described above, Laminin 511E8. As a result, PSA-NCAM-positive cells and Corin-positive cells were obtained with each of the coating agents, but the use of Laminin 511E8 resulted in a smaller number of remaining undifferentiated cells (Tra-1-60-positive cells) and the highest proportion of Corin-positive cells (FIG. 2). Thus, it was found that, by performing adherent culture with Laminin 511E8 coating, a larger number of cells can be handled at one time, and a higher proportion of desired cells can be achieved. Laminin 511E8 was used as the coating agent in the following experiments.

An anti-Corin antibody was prepared by the following method. First, from the Corin gene of *Macaca fascicularis*, a gene sequence encoding a part of the extracellular domain (79th-453rd amino acids) was introduced into 293E cells, and the cells were then allowed to express the extracellular-domain fragment of Corin protein, followed by recovery the protein. A mouse was immunized with the recovered protein, and lymphocytes were then extracted and fused with myeloma cells. From the cell population after the fusion, a clone having reactivity with Corin was selected. The culture supernatant of the clone was used as the anti-Corin monoclonal antibody.

Five days after the culture in Basal Medium A supplemented with 0.1 μM LDN193189 and 3 μM CHIR99021 (Day 12), the cells were dissociated using TrypLE CTS, and suspended in Ca$^{2+}$Mg$^{2+}$-free HBSS (Invitrogen) supplemented with 2% FBS, 10 μM Y-27632 (WAKO), 20 mM D-glucose, and 50 μg/ml penicillin/streptomycin. The anti-Corin antibody was added to the suspension, and the resulting mixture was incubated at 4° C. for 20 minutes, followed by sorting the cells using FACSAria II (BD) to collect Corin-positive cells.

The collected Corin-positive cells were transferred to a Lipidure-coat 96 well plate (NOF Corporation) in an amount of 20,000 cells/well, and subjected to suspension culture in Basal Medium B (Neurobasal medium (Invitrogen) supplemented with B27 Supplement (without vitamin A: Invitrogen), 20 ng/mL BDNF, 10 ng/mL GDNF, 200 mM ascorbic acid, and 0.4 mM dbcAMP (Sigma)). In this suspension culture, the initial medium was supplemented with 30 μM Y-27632, but a half volume of the initial medium was replaced with Y-27632-free medium once every three days. Cells obtained 16 days after the sorting (Day 28), and cells obtained by continuing the suspension culture for additional 14 days (Day 42), were evaluated for whether they are suitable for transplantation. During the suspension culture, a half volume of the medium was replaced once every three days. The scheme of this culture method is shown in FIG. 1.

In addition, suspension culture was carried out in the same manner as described above except that the sorting for Corin on Day 12 was not carried out, to provide a control.

Study of Schedule of Sorting

Figure 3:
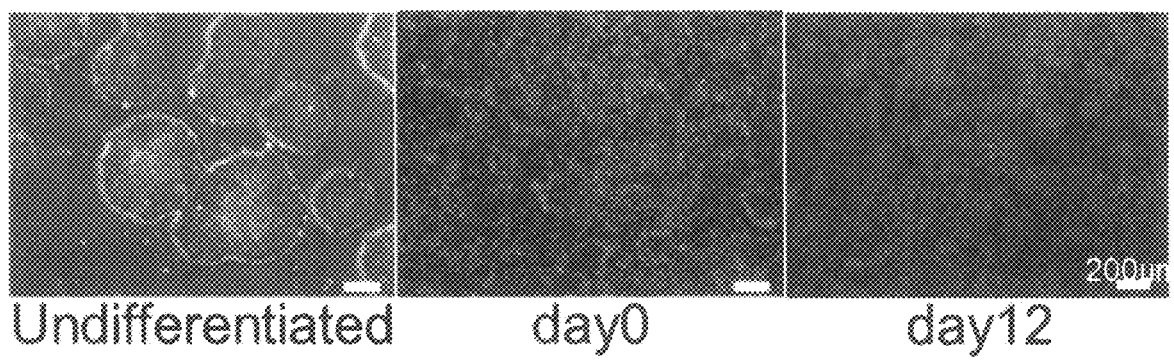
FIG. 3 shows phase-contrast images (photographs) of human iPS cells (836B3) and the cells during a differentiation induction process. An image obtained before the differentiation induction (left panel), an image obtained immediately after the differentiation induction (day0) (middle panel), and an image obtained 12 days after the induction (day 12) (right panel) are shown.
Figure 4:
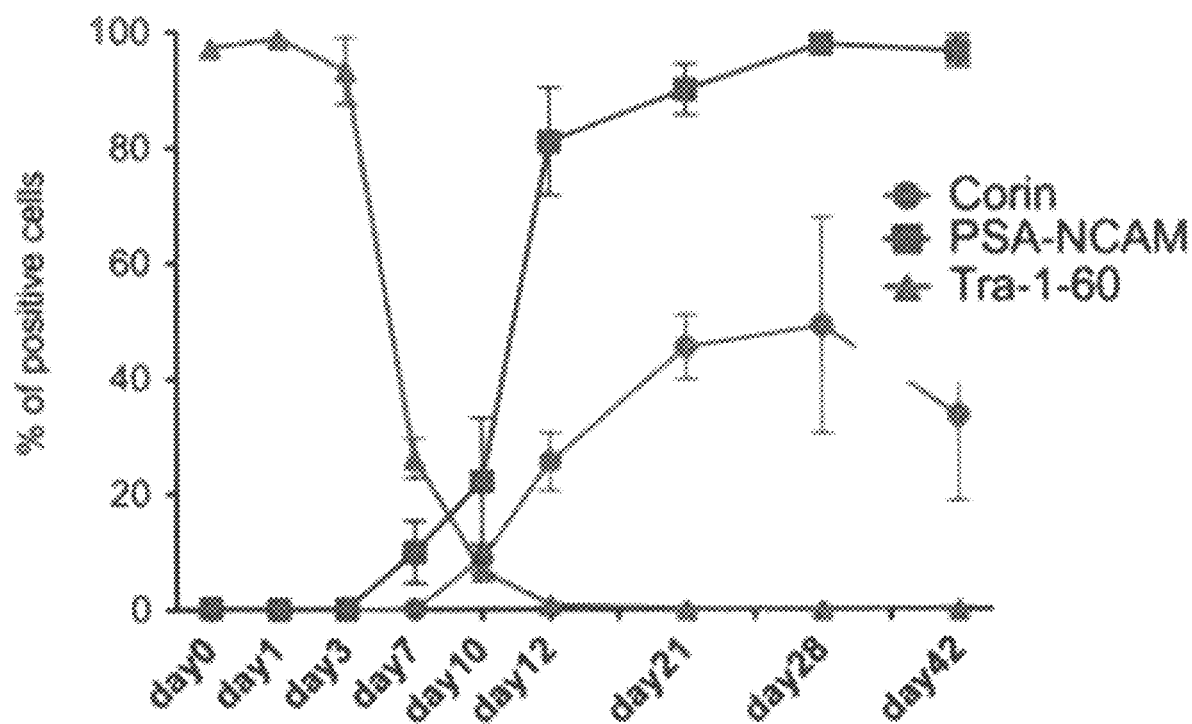
FIG. 4 shows changes in the proportions of Corin-positive cells (circle), PSA-NCAM-positive cells (square), and Tra-1-60-positive cells (triangle). On Day 12 and later, the results were obtained under conditions without sorting.

FIG. 3 shows images of cells obtained from iPS cells (836B3) by the method described above, which images were taken at different times during the differentiation induction. FIG. 4 shows the proportions of Corin-positive cells, polysialylated (PSA)-NCAM-positive cells, and Tra-1-60-positive cells obtained by performing no sorting on Day 12, transferring cell clusters obtained on Day 28 to a dish coated with poly-L-ornithine, fibronectin, and laminin, and performing culture in Basal Medium B for additional 14 days (Day 42). In this differentiation induction method, the proportion of cells positive for PSA-NCAM, which is a neural cell marker, increased from Day 7, and these cells became the majority on Day 12 or near Day 12. Cells positive for Corin, which is a floor plate marker, appeared on Day 10, and reached the peak between Days 21 to 28. The same trend was observed also in the case where 404C2 was used. Thus, it was suggested that, in cases where Corin-positive cells are obtained by sorting, the sorting is preferably carried out on Day 10 or later.

Subsequently, expression of Oct4, Nanog, Sox1, Sox17, Brachyury, hGSC, and the like until Day 12 was measured by quantitative PCR. Their changes with time were as shown in FIG. 5A. The expression of SOX1 increased in an early phase, and was maintained thereafter. The expression of undifferentiation markers Oct4 and Nanog showed decreases. The expression of Brachyury, which is a mesodermal marker, transiently increased, and then decreased. The expression of SOX17, which is an endodermal marker, was constantly low. FIG. 5B shows changes in the expression of Oct4, Map2ab, Lmx1a, En1, Nurr1, TH, and Foxa2 measured with time in the cells obtained by performing no sorting on Day 12, transferring cell clusters obtained on Day 28 to a dish coated with poly-L-ornithine, fibronectin, and laminin, and performing culture in Basal Medium B for additional 14 days (Day 42). The expression levels of the markers described above other than TH were found to have reached the plateau on Day 12. The same trend was observed also in the case where 404C2 was used.

Figure 6:
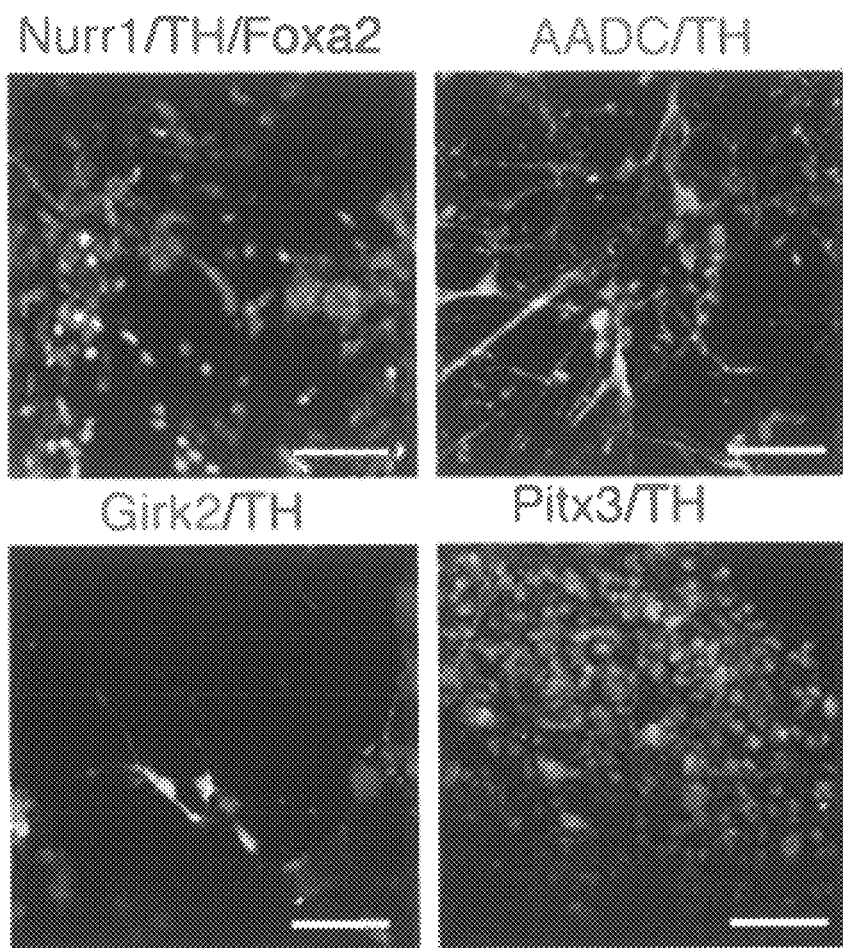
FIG. 6 shows immunostaining images (photographs) of cells on Day 42 during culture on a poly-L-ornithine/laminin/fibronectin coating.

The cells on Day 42 obtained without performing sorting were subjected to immunostaining against TH (marker for dopaminergic neural cells) and against Foxa2 and Nurr1 (both are markers for midbrain). As a result, 40% of the cells were positive for TH, and its coexpression with Foxa2 and Nurr1 was found. The TH-positive cells were also found to exhibit coexpression of AADC, Pitx3, and Girk2, which are other markers for dopaminergic neural cells (FIG. 6).

Effect of Sorting Using Corin as Index

Figure 8:
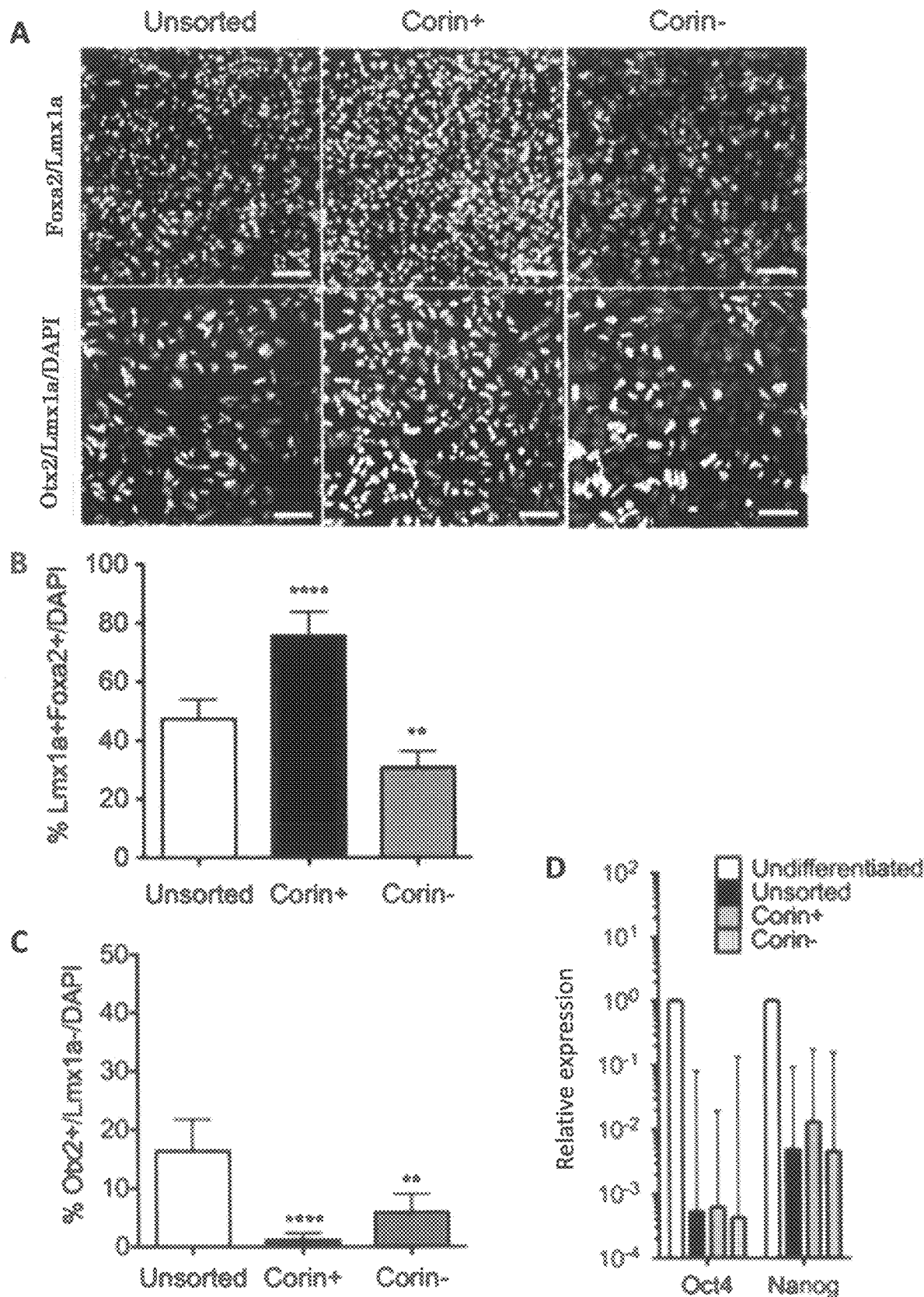
FIG. 8 shows results of analysis of gene expression on Day 12 in Corin-positive cells (Corin$^+$) and Corin-negative cells (Corin$^-$) obtained by sorting using an anti-Corin antibody, and unsorted cells (Unsorted).

In the same manner as described above, expression of each marker gene in the cells immediately after the sorting on Day 12 was measured by PCR (FIG. 7A). As a result, the Day 12-Corin-positive cells showed higher expression of not only Corin, but also midbrain markers Lmx1a and En1 as well as a floor plate marker Foxa2, compared to the unsorted cells. On the other hand, those cells showed lower expression of a hindbrain marker Gbx2 and a forebrain marker Six3, compared to the unsorted cells. A similar trend was observed also in the case of 404C2. Comparison by comprehensive expression analysis was made between the case where the sorting was carried out on Day 12 and the case where the sorting was not carried out. As a result, higher expression of a rostral marker Pax6, caudal marker Foxa2, early nerve marker Neurog2, postmitotic neural cell marker NEFM (not shown in the figure), and nonneuronal cell markers DLK1 and CYP1B1, was observed in the unsorted cells (FIG. 7B). As a result of additional immunostaining, an increased proportion of Lmx1a/Foxa2-co-positive cells was found among Corin-positive cells (FIGS. 8A and 8B; 75.52±8.255% vs. 47.37±6.624%). On the other hand, cells positive for Otx2, which is expressed in the rostral side of the midbrain/hindbrain boundary, and negative for Lmx1a, were found to be decreased in the sorted cells (FIG. 8C). No large difference was found in the expression of undifferentiation markers Oct4 and Nanog (FIG. 8D).

Subsequently, a similar study was carried out for the cells immediately after the sorting on Day 21. Although the proportion of Corin-positive cells was higher in the case of sorting on Day 21 (45.47±47.61% (day21) vs. 18.97±15.49% (day12)), the expression levels of Lmx1a and Foxa2 did not show any change due to the sorting on Day 21 (FIG. 9A). Similarly, in the immunostaining, the proportion of Lmx1a/Foxa2-co-positive cells among Corin-positive cells did not show a significant difference between the cell population obtained by carrying out the sorting on Day 21 and the unsorted cell population (FIGS. 9B and 9C).

From these results, it was found that sorting on Day 12 is more preferred than sorting on Day 21.

Culture Period after Sorting

Figure 11:
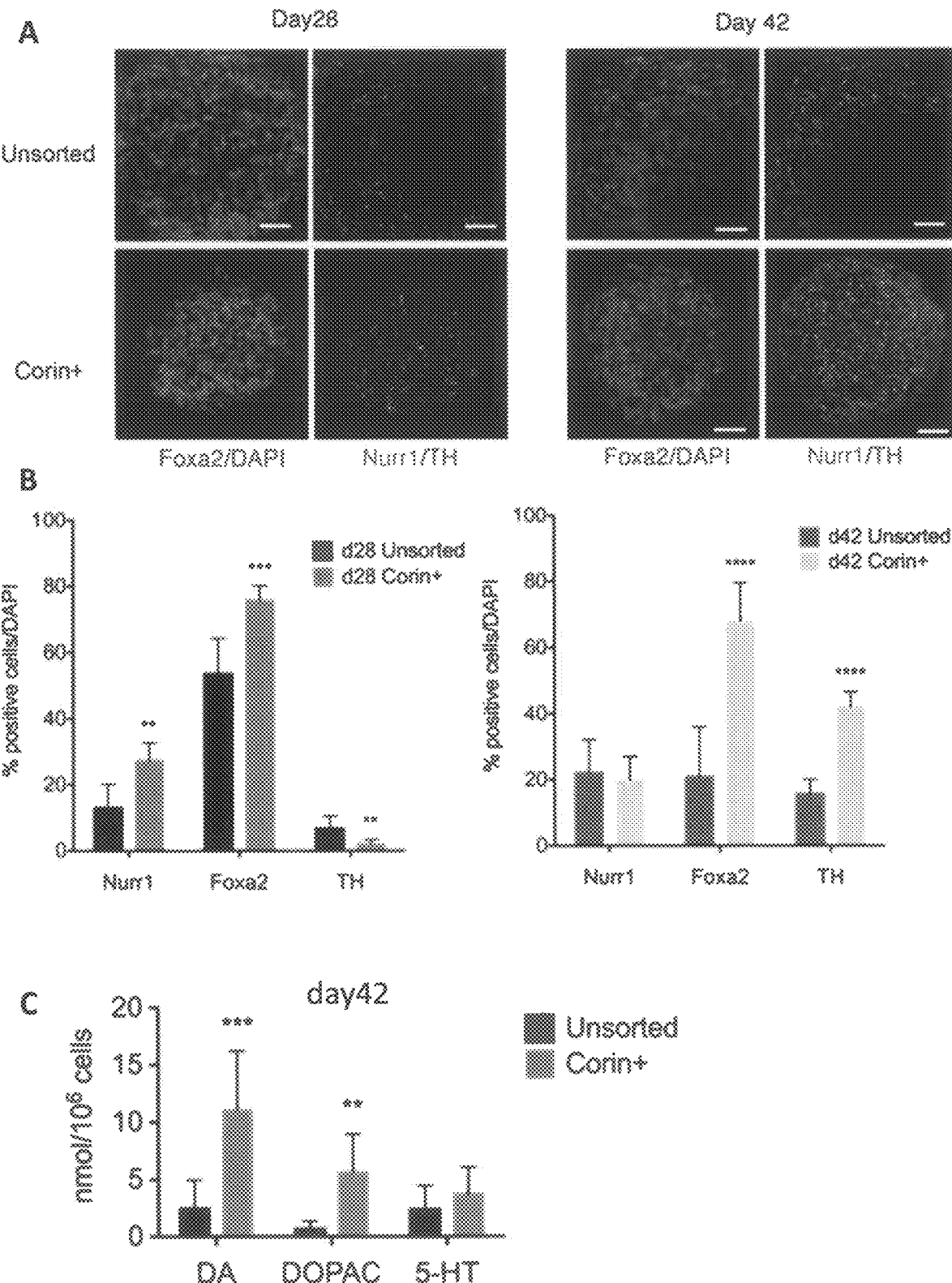
FIG. 11 shows results of analysis of gene expression on Day 28 (day28) and Day 42 (day42) after the differentiation induction.

Cells on Day 28 and Day 42 induced by the culture method described above were studied on the difference in the degree of maturation of dopaminergic neural cells depending on whether the sorting for Corin-positive cells on Day 12 was carried out or not. On Day 28 and Day 42, the sphere size of the Corin-positive cells was found to be smaller compared to that of unsorted cells (FIGS. 10A and 10B). As a result of immunostaining on Day 28 and Day 42, the proportion of Foxa2-positive cells in the case where the Day-12 sorting was carried out was found to be 70 to 75%, and higher than that in the case where no sorting was carried out (FIGS. 11A and 11B). The proportions of Nurr1-positive cells and TH-positive cells were 27.34±5.511% and 2.098±1.243%, respectively, on day 28, and 19.91±6.966% and 42.04±4.481%, respectively, on day 42. Thus, the proportion of TH-positive cells was higher on Day 42 than on Day 21. As a result of HPLC quantification of dopamine (DA), 3,4-dihydroxyphenyl acetic acid (DOPAC), and serotonin (5-HT) released into the medium due to stimulation by high potassium chloride on Day 42, the amounts of DA and DOPAC released were found to be significantly larger in the case where the cells were subjected to the Corin sorting, compared to the case where the Corin sorting was not carried out (FIG. 11C).

Figure 12:
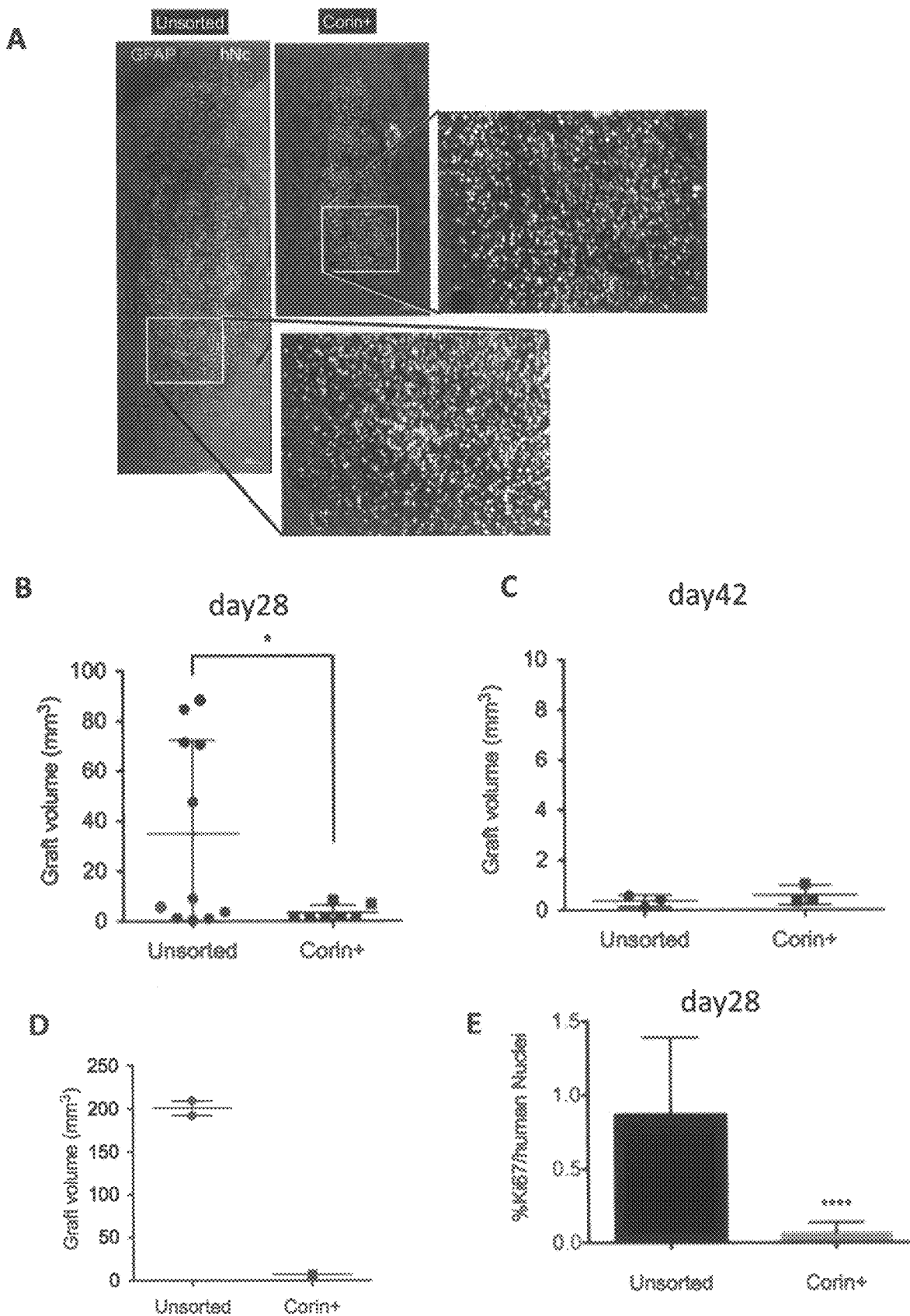
FIG. 12 shows the states of transplants at Week 16 after intracerebral transplantation of cells obtained by culturing Corin-positive cells collected by sorting (Day 12) (Corin$^+$), or cells induced without sorting (Unsorted), to rats (to which 6-hydroxydopamine (6-OHDA) was administered) on Day 28 after differentiation induction.

Subsequently, suspension culture was carried out using the cells that were subjected to the Corin sorting on Day 12 or the cells that were not subjected to the Corin sorting. On Day 28 or Day 42, $4\times10^5$ cells were suspended in 2 μl of physiological saline, and administered into the striate body of the cerebrum of model rats for Parkinson's disease (rats to which 6-OHDA was administered) using a 22-gauge injection needle. At Week 16, observation of the transplants was carried out (FIG. 12A). As a result of measurement of the sizes of the transplants derived from the Day-28 cells, the transplants were found to have almost the same size (8.5 to 1.5 $mm^3$) in the case where the sorting for Corin-positive cells was carried out (FIG. 12B). On the other hand, the transplants were found to have large variation in size (88.4 to 0.5 $mm^3$) in the case where the Corin sorting was not carried out. A significant difference was found in the mean size between these cases (34.96±37.52 $mm^3$ (unsorted) vs 3.45±2.932 $mm^3$ (sorted)) (FIG. 12B). In addition, suspension culture was carried out using the cells that were subjected to the Corin sorting on Day 12 or the cells that were not subjected to the Corin sorting, and the cells were then similarly administered to model rats for Parkinson's disease after seven days of the culture (Day 19). As a result, the sizes of the transplants were found to be significantly smaller in the sorted group (FIG. 12D). As a result of quantification of the proportion of Ki67-positive cells in the transplants, the proportion was found to be as low as not more than 1% irrespective of whether the sorting was carried out or not. However, the proportion was significantly lower in the cells that were subjected to the Corin sorting (FIG. 12E). On the other hand, in the cases of Day 42, the sizes of the transplants were not more than 1 mm³ irrespective of whether the sorting was carried out or not (FIG. 12C), and no Ki67-positive cells were found.

Figure 14:
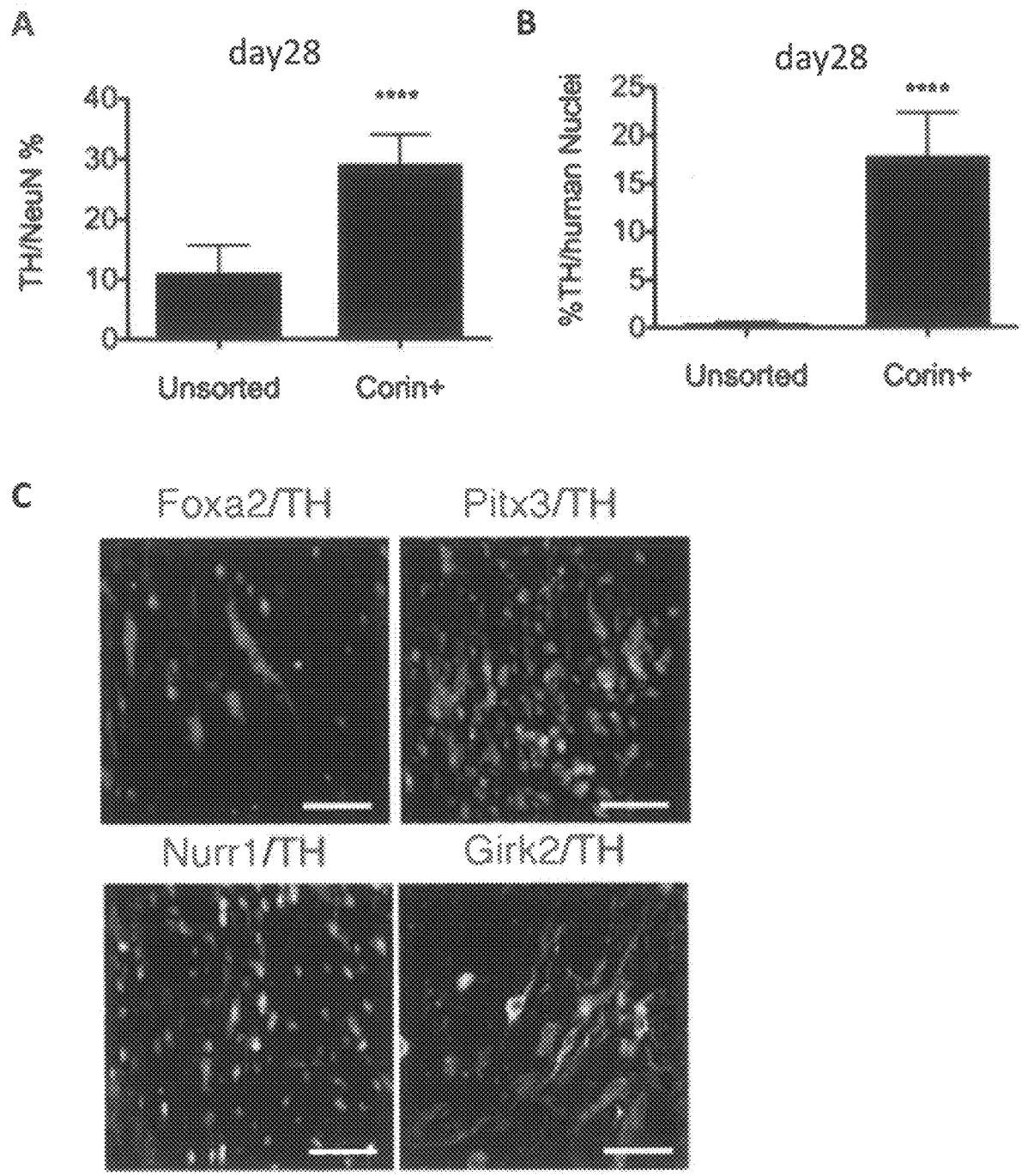
FIG. 14 shows results of analysis of transplants in the cases of transplantation of the cells on Day 28.
Figure 15:
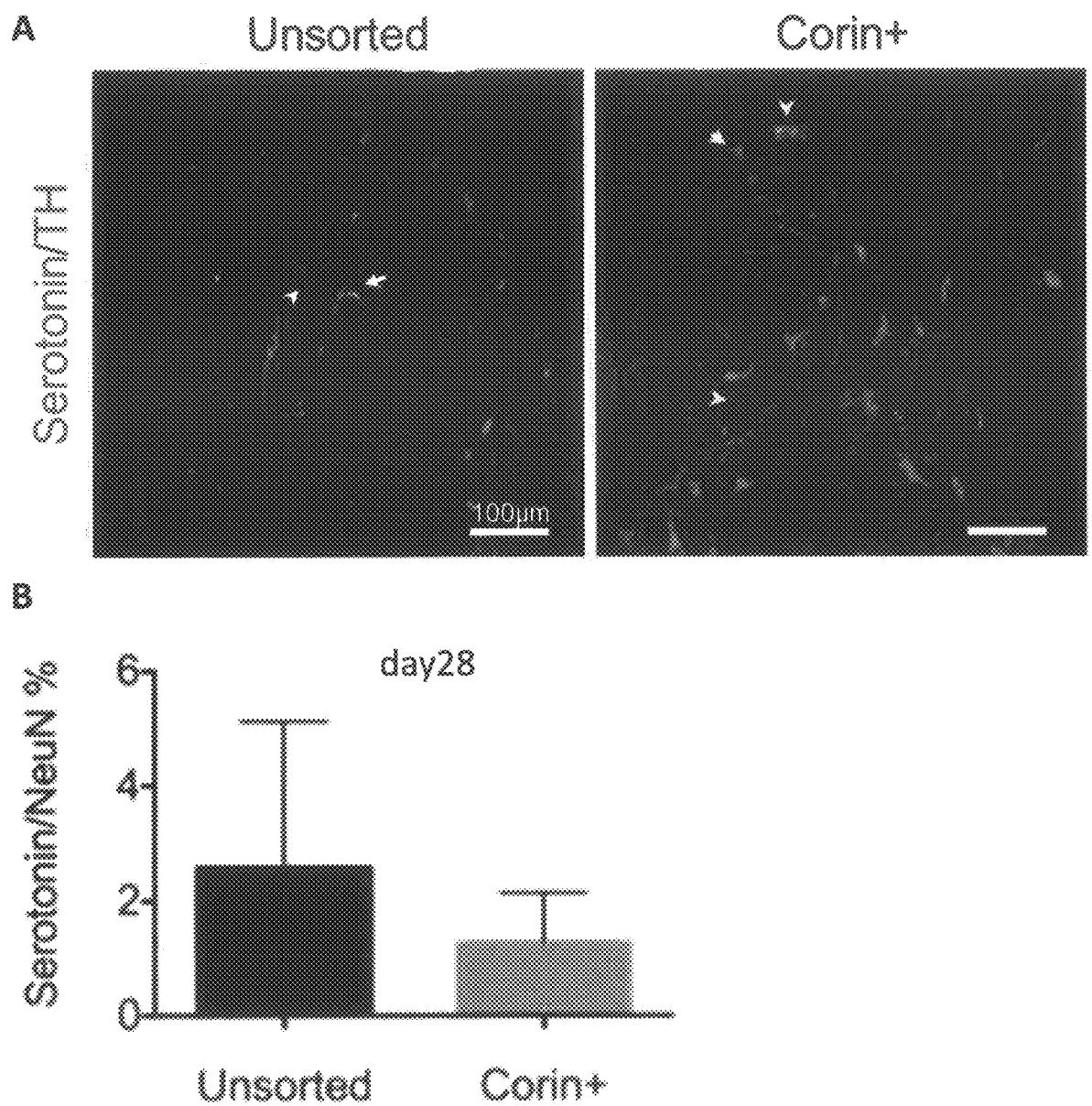
FIG. 15 shows results of intracerebral transplantation of cells obtained by culturing Corin-positive cells collected by sorting (day 12) (Corin$^+$), or cells induced without sorting (Unsorted), to rats (to which 6-OHDA was administered) on Day 28 (day28) after the differentiation induction.

Subsequently, circling due to amphetamine induction, which is caused by left-right imbalance of the dopamine level, was studied. As a result, the group to which the cells sorted for Corin-positive cells on Day 12 were administered (Day 28) and the group to which the unsorted cells were administered (Day 28) both showed significantly lower numbers of times of circling compared to a group to which the cells were not administered (administration of only the medium). At Week 16 after the administration of the cells, the changes in the behavior were not significantly different between the case where the sorting was carried out and the case where the sorting was not carried out (FIG. 13A). As a result of observation of TH-positive cells in the transplants at this time, it was found that a significantly larger number of TH-positive cells were remaining in the case where the cells sorted for Corin were transplanted (FIGS. 13B and 13C; 6747±2341 cells/graft (sorted) vs. 3436±2384 cells/graft (unsorted)). At this time, the number of TH-positive cells per number of NeuN-positive cells (total nerve cells), as well as the number of TH-positive cells per number of hNc-positive cells (total surviving cells), were significantly higher in the case where the sorting was carried out (FIGS. 14A and 14B). Coexpression of other markers for dopaminergic cells (Foxa2, Nurr1, and Pitx3) was also found. Girk2, which is a marker for A9 dopaminergic cells in the substantia nigra pars compacta, was also positive in a half of the cells (FIG. 14C). As a result of observation of the number of serotonin cells, the proportion of these cells was found to be low in both cases (FIGS. 15A and 15B).

On the other hand, when the cells that were sorted for Corin-positive cells on Day 12 and the unsorted cells were similarly administered (Day 42), no significant difference in amelioration of the abnormal circling was found between these cells (FIG. 13D). Similarly, these cells showed no significant difference in the number and concentration of TH-positive cells in the transplant (FIGS. 13E and 13F). In correlation with these results, the mean number of surviving TH-positive cells was 6747±2341 cells/graft in the case of transplantation on Day 28 (FIG. 13B), while the mean number was 1431±753.7 cells/graft in the case of transplantation on Day 42 (FIG. 13E). Thus, the number of surviving cells tended to be larger in the case of transplantation on Day 28.

Subsequently, comparisons were made by microarray analysis between the cells on Day 28 subjected to the Day-12 sorting and the unsorted cells on Day 28, and between the cells on Day 28 subjected to the Day-12 sorting and the cells on Day 42 subjected to the Day-12 sorting (FIG. 16A). The unsorted cells on Day 28 were found to show higher expression of PAX6, which is a forebrain marker. On the other hand, the sorted cells were found to show high expression of ALCAM. In the comparison between the cells on Day 28 and the cells on Day 42, the cells on Day 28 showed higher expression of SHH, WNT5A, and CORIN. On the other hand, the cells on Day 42 showed higher expression of TH.

A comparison was made between fetal ventral mesencephalic cells (7 weeks old), which have been clinically used for Parkinson's disease so far, and cells on Day 28 and Day 42 which were subjected to sorting for Corin-positive cells on Day 12. The fetal ventral mesencephalic cells showed higher expression of TH and PITX3, which are markers for dopaminergic neural cells (not shown in the figure), relative to the cells on Day 28. The fetal ventral mesencephalic cells also showed higher expression of TPH2, which is a marker for serotonergic nerve cells (FIG. 16B). As a result of hierarchical cluster analysis, the fetal ventral mesencephalic cells were found to show higher similarity to the cells on Day 42 (FIG. 16C). Since the cells on Day 28 show expression of genes associated with axon guidance (SPON1 and SLIT2), it was suggested that the cells are at an earlier developmental stage than fetal ventral mesencephalic cells.

From the above results, it was suggested that, by using cells (Day 28) prepared by selecting Corin-positive cells and subjecting the selected cells to suspension culture for 16 days, the growth of the transplant and the survival of dopaminergic cells can be increased, so that such cells are suitable for use in treatment of Parkinson's disease.

Example 2

Cell Culture

ES cells (Kh-ES1) were dissociated using TrypLE CTS (Life Technologies), and the whole cells were transferred to a 6-well plate coated with Laminin 511E8. The cells were then cultured in Basal Medium A (GMEM supplemented with 8% KSR, 1 mM sodium pyruvate, 0.1 mM MEM non-essential amino acid, and 0.1 mM 2-mercaptoethanol) supplemented with 10 μM Y-27632, 0.1 μM LDN193189, and 0.5 μM A83-01. One day after the beginning of the culture (Day 1), the medium was replaced with Basal Medium A supplemented with 0.1 μM LDN193189, 0.5 μM A83-01, 2 μM purmorphamine, and 100 ng/mL FGF8. Three days after the beginning of the culture (Day 3), the medium was replaced with Basal Medium A supplemented with 0.1 μM LDN193189, 0.5 μM A83-01, 2 μM purmorphamine, 100 ng/mL FGF8, and 3 μM CHIR99021. Seven days after the beginning of the culture (Day 7), the medium was replaced with Basal Medium A supplemented with 0.1 μM LDN193189 and 3 μM CHIR99021. On Day 12 (12 days after the beginning of the culture), the medium was replaced with Neurobasal medium (Invitrogen) supplemented with B27 Supplement (without vitamin A), 2 mM L-glutamine, 20 ng/mL recombinant human (rh) BDNF, 10 ng/mL rhGDNF, 400 μM dbcAMP (Sigma), and 200 μM ascorbic acid. Unless otherwise specified, medium replacement was carried out every day using the same composition as that used on the previous day.

On Day 14 (14 days after the beginning of the culture), the cells were dissociated using TrypLE CTS, and subjected to sorting using a FACS with an anti-Lrtm1 antibody (WO 2013/015457), to recover Lrtm1-positive cells.

The recovered Lrtm1-positive cells were transferred to a Lipidure-coat 96 well plate (Thermo) in an amount of 20,000 cells/well, and subjected to suspension culture using Neurobasal medium supplemented with 30 μM Y-27632, B27 Supplement (without vitamin A), 2 mM L-glutamine, 20 ng/mL recombinant human (rh) BDNF, 10 ng/mL rhGDNF, 400 μM dbcAMP, 1% KSR, penicillin/streptomycin (Gibco), and 200 μM ascorbic acid. Thereafter, a half volume of the medium was replaced with Y-27632-free medium once every three days. The cells were used in experiments 7 days after the sorting (Day 21) or 21 days after the sorting (Day 35).

Effect of Sorting Using Lrtm1 as Index (Immunostaining)

Based on investigation of the cells on Day 21 by immunostaining, the proportion of Foxa2-positive cells was 87.4%; the proportion of Lmx1a-positive cells was 87.5%;

and the proportion of Foxa2-positive/Lmx1a-positive cells was 82.7% (FIG. 17A). Based on comparison on Day 35 between the cells subjected to the sorting and the unsorted cells, it was found that the proportions of Foxa2-, Nurr1-, and TH-positive cells were higher in the cells subjected to the sorting for Lrtm1 (FIG. 17B).

Effect of Sorting Using Lrtm1 as Index (Cell Transplantation)

Figure 18:
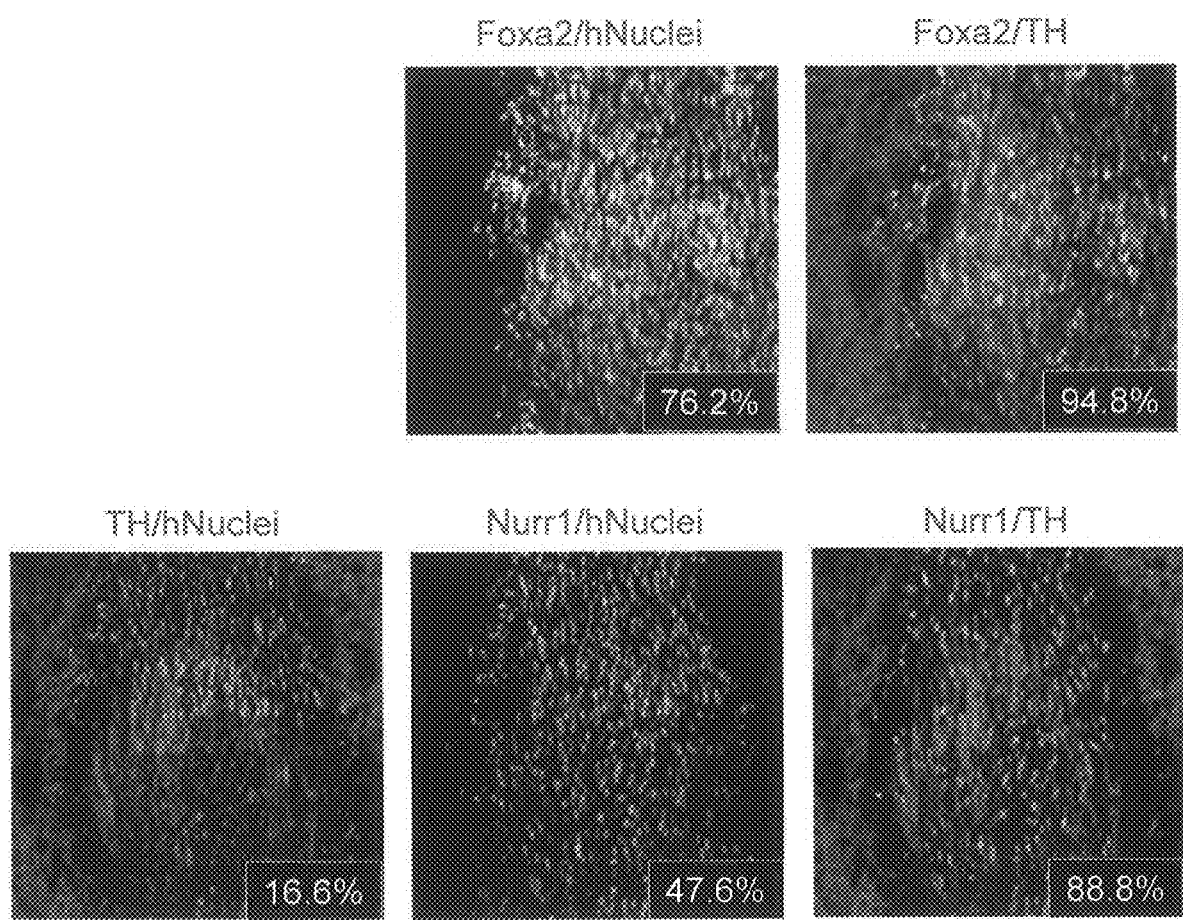
FIG. 18 shows immunostaining images (photographs) of transplants for markers (Foxa2, TH, and Nurr1), which images were taken after transplantation of the cells obtained by one-day culture of Lrtm1-positive cells collected by sorting (Day 14) to SD rats of 10 weeks old.

On the next day of the sorting for Lrtm1 (Day 15), 10 to $15 \times 10^4$ cells/tract were administered into the brain of SD rats of 10 weeks old, followed by observation at Week 4 after the administration. As a result, survival of Foxa2-, TH-, and Nurr1-positive cells derived from the transplanted (human-derived) cells was observed (FIG. 18).

Example 3

Cell Culture

ES cells (Kh-ES1) were dissociated using TrypLE CTS (Life Technologies), and $4 \times 10^5$ cells were then transferred to a 6-well plate coated with Laminin 511E8. The cells were then cultured in StemFit medium (Ajinomoto) supplemented with 10 µM Y-27632. Four days later, the medium was replaced with the above-described Basal Medium A supplemented with 0.1 µM LDN193189 and 0.5 µM A83-01 (Day 0). One day after the beginning of the culture (Day 1), the medium was replaced with Basal Medium A supplemented with 0.1 µM LDN193189, 0.5 µM A83-01, 2 µM purmorphamine, and 100 ng/mL FGF8. Three days after the beginning of the culture (Day 3), the medium was replaced with Basal Medium A supplemented with 0.1 µM LDN193189, 0.5 µM A83-01, 2 µM purmorphamine, 100 ng/mL FGF8, and 3 µM CHIR99021. Seven days after the beginning of the culture (Day 7), the medium was replaced with Basal Medium A supplemented with 0.1 µM LDN193189 and 3 µM CHIR99021. On Day 14 (14 days after the beginning of the culture), the cells were sorted, or the medium was replaced with Neurobasal medium (Invitrogen) supplemented with B27 Supplement (without vitamin A), 2 mM L-glutamine, 20 ng/mL recombinant human (rh) BDNF, 10 ng/mL rhGDNF, 400 µM dbcAMP (Sigma), and 200 µM ascorbic acid. Unless otherwise specified, medium replacement was carried out every day using the same composition as that used on the previous day.

Sorting

The cells were cultured by the method described above, and dissociated on Day 14 (14 days after the beginning of the culture) or Day 21 (21 days after the beginning of the culture) using TrypLE CTS. The cells were then sorted using a FACS with an anti-Lrtm1 antibody (WO 2013/015457), to recover Lrtm1-positive cells.

The recovered Lrtm1-positive cells were transferred to a Lipidure-coat 96 well plate (Thermo) in an amount of $2 \times 10^4$ cells/well, and subjected to suspension culture using Neurobasal medium supplemented with 30 µM Y-27632, B27 Supplement (without vitamin A), 2 mM L-glutamine, 20 ng/mL recombinant human (rh) BDNF, 10 ng/mL rhGDNF, 400 µM dbcAMP, 1% KSR, penicillin/streptomycin (Gibco), and 200 µM ascorbic acid. Thereafter, a half volume of the medium was replaced with Y-27632-free medium once every three days. The cells were used in experiments 7 days or 14 days after the sorting.

Effect of Sorting Using Lrtm1 as Index (Immunostaining)

Figures 1, 19:
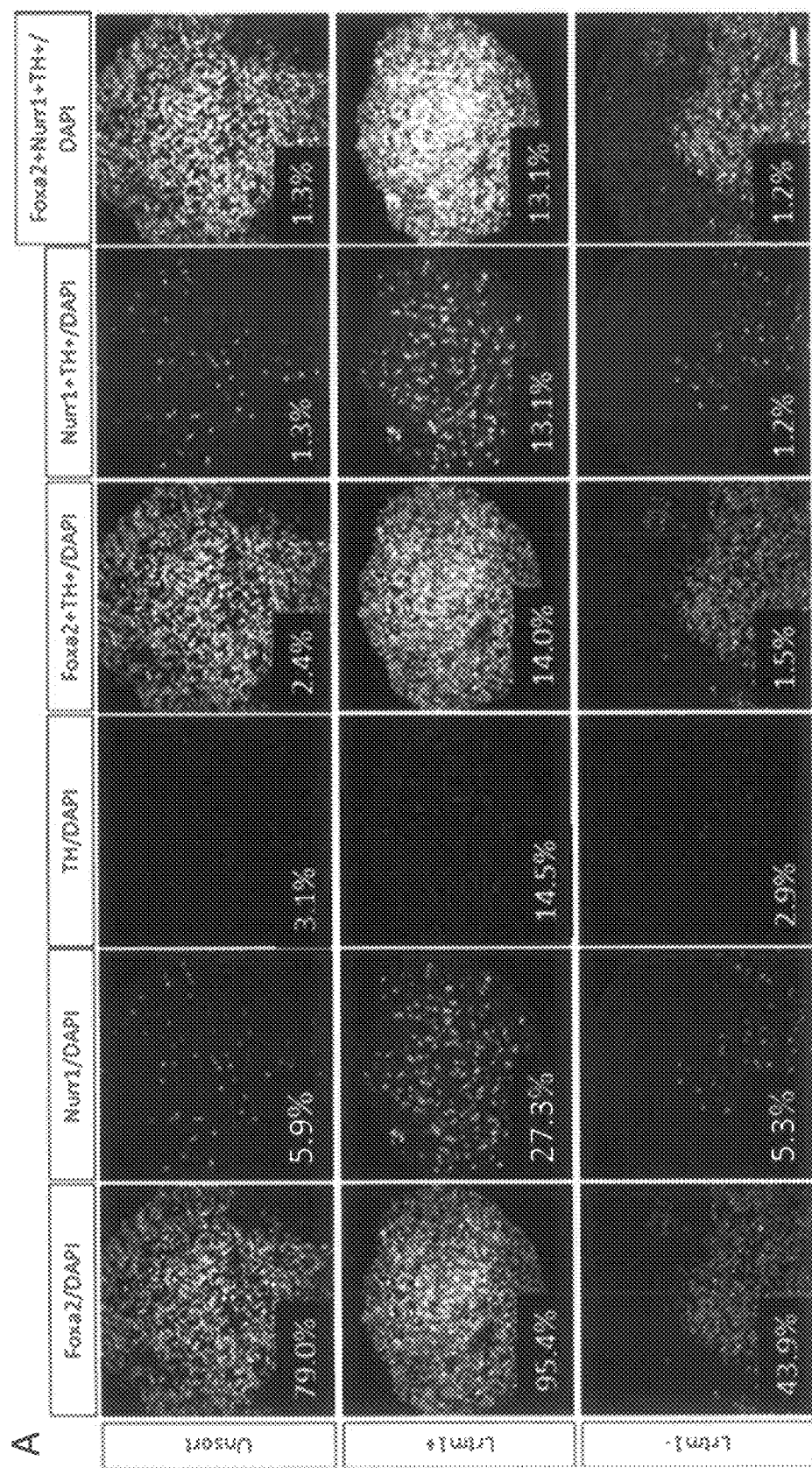
Figures 3, 19:
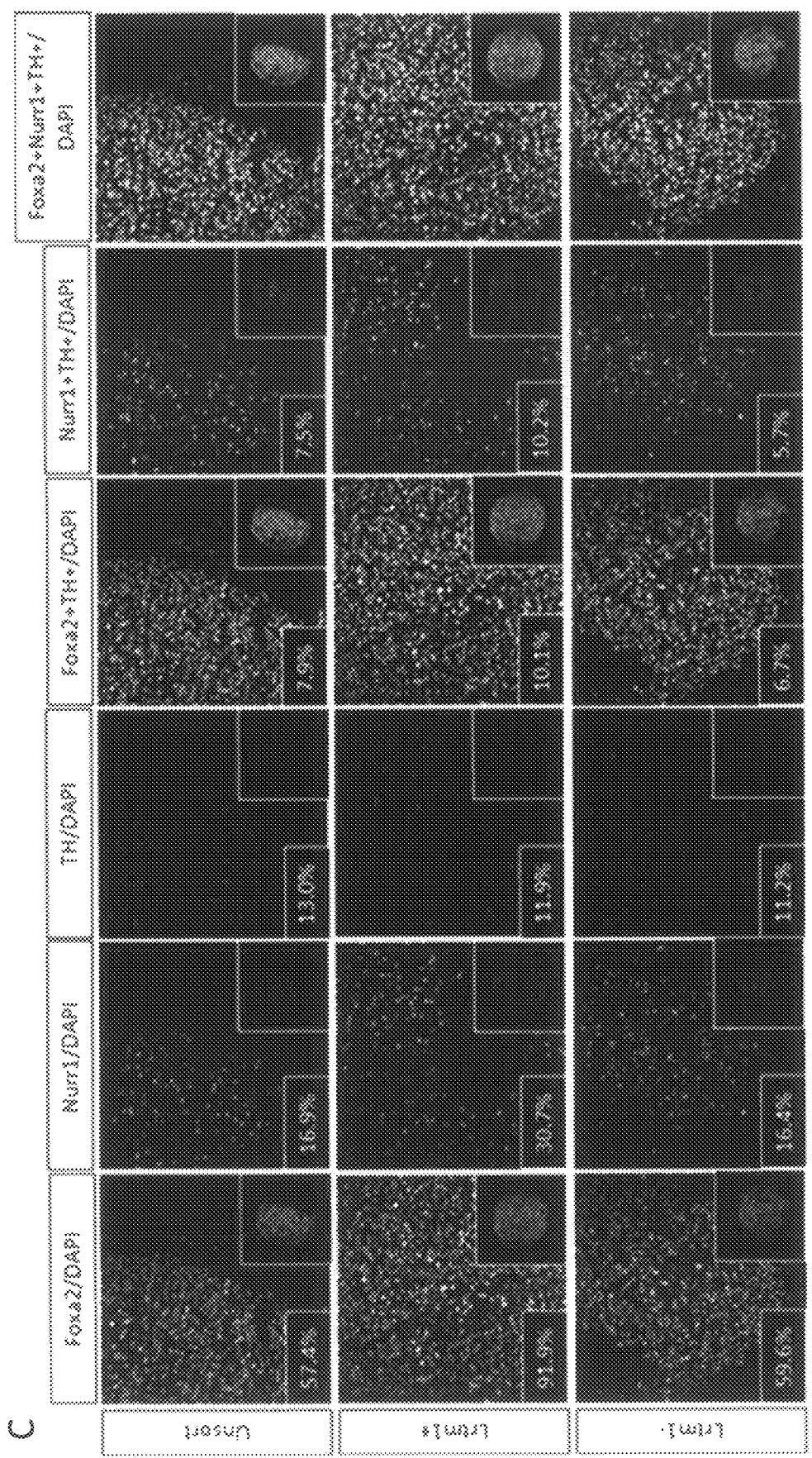

Investigation by immunostaining (Foxa2, Nurr1, and TH) was carried out for the cells of 14 day-7 day (sorting on Day 14, followed by 7 days of culture), 14 day-14 day (sorting on Day 14, followed by 14 days of culture), and 21 day-7 day (sorting on Day 21, followed by 7 days of culture). As a result, the proportion of Foxa2-positive cells was found to be not less than 90% under any of the above conditions, but the proportion of Nurr1-positive/TH-positive cells was 13.1%, 24.0%, and 10.2% in the cases of 14 day-7 day, 14 day-14 day, and 21 day-7 day, respectively (FIG. 19). Thus, the proportion of Foxa2, Nurr1, and TH-positive cells was highest in the case of 14 day-14 day.

Based on the results described above, it was shown that the timing of the sorting is preferably Day 14 rather than Day 21 after the beginning of the differentiation induction, and that the culture period after the sorting is preferably 14 days rather than 7 days.

INDUSTRIAL APPLICABILITY

The present invention is useful for regenerative medicine, especially for treatment of Parkinson's disease.

What is claimed is:

1. A method for producing dopaminergic neuron progenitor cells from pluripotent stem cells, said method comprising the steps of:
   (a) culturing pluripotent stem cells on an extracellular matrix in a medium containing a BMP inhibitor and a TGFβ inhibitor for at least one day, wherein said extracellular matrix is laminin or a fragment(s) thereof;
   (b) replacing the medium from Step (a) with a medium containing a BMP inhibitor, a TGFβ inhibitor, a SHH signal-stimulating agent, and FGF8 and further culturing the cells for at least one day;
   (c) replacing the medium from Step (b) with a medium containing a BMP inhibitor, a TGFβ inhibitor, a SHH signal-stimulating agent, FGF8, and a GSK3β inhibitor and further culturing the cells for at least one day;
   (d) replacing the medium from Step (c) with a medium containing a BMP inhibitor and a GSK3β inhibitor and further culturing the cells for at least one day; and
   (e) suspending the cells obtained in Step (d);
   (f) collecting Corin- and/or leucine-rich repeats and transmembrane domains 1 (Lrtm1) positive cells from the cells obtained in Step (e) using an antibody that binds to Corin and/or an antibody that binds to Lrtm1; and
   (g) culturing the cells obtained in Step (f) in suspension in a medium containing a neurotrophic factor, wherein Step (g) is carried out for at least 7 days, and
   wherein Steps (a)-(e) are performed within 10 to 21 days.

2. The method according to claim 1, wherein said neurotrophic factor is BDNF and GDNF.

3. The method according to claim 1, wherein the medium in Step (g) further comprises B27 supplement, ascorbic acid, and dibutyryl cyclic AMP.

4. The method according to claim 1, wherein said Steps (a-e) is carried out for 12 days to 21 days.

5. The method according to claim 1, wherein said Step (g) is carried out for 14 days to 30 days.

6. The method according to claim 1, wherein said extracellular matrix is laminin 511E8.

7. The method according to claim 1, wherein said BMP inhibitor is selected from the group consisting of Chordin, Noggin, Follistatin, Dorsomorphin and LDN193189, wherein said TGFβ inhibitor is selected from the group consisting of Lefty-1, SB431542, SB202190, SB505124, NPC30345, SD093, SD908, SD208, LY2109761, LY364947, LY580276 and A83-01, wherein said SHH signal-stimulating agent is selected from the group consisting of SHH, Hh-Ag1.5, SAG, 20a-hydroxycholesterol and purmorphamine, and wherein said GSK3β inhibitor is selected from the group consisting of BIO, 6-bromoindirubin-3'-oxime, SB216763, GSK-3β inhibitor VII, L803-mts and CHIR99021.

8. The method according to claim 1, wherein said BMP inhibitor is LDN193189, wherein said TGFβ inhibitor is A83-01, wherein said SHH signal-stimulating agent is purmorphamine, and wherein said GSK3β inhibitor is CHIR99021.

* * * * *

UNITED STATES PATENT AND TRADEMARK OFFICE
CERTIFICATE OF CORRECTION

PATENT NO.        : 11,473,058 B2                                        Page 1 of 1
APPLICATION NO.   : 14/916696
DATED             : October 18, 2022
INVENTOR(S)       : Takahashi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 393 days.

Signed and Sealed this
First Day of August, 2023

Katherine Kelly Vidal
*Director of the United States Patent and Trademark Office*